United States Patent
Nishioka et al.

(10) Patent No.: US 9,610,279 B2
(45) Date of Patent: *Apr. 4, 2017

(54) METHOD FOR INDUCTION OF A HEAT SHOCK PROTEIN, ANTI-STRESS OR REGULATION OF AN AUTONOMIC NERVE

(71) Applicant: AMINO UP CHEMICAL CO., LTD., Hokkaido (JP)

(72) Inventors: Hiroshi Nishioka, Hokkaido (JP); Tomohiro Ito, Hokkaido (JP); Takahiro Maeda, Hokkaido (JP)

(73) Assignee: AMINO UP CHEMICAL CO., LTD., Sapporo-Shi, Hokkaido (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/080,899

(22) Filed: Mar. 25, 2016

(65) Prior Publication Data

US 2016/0193184 A1 Jul. 7, 2016

Related U.S. Application Data

(63) Continuation of application No. 14/366,276, filed as application No. PCT/JP2012/083040 on Dec. 20, 2012, now Pat. No. 9,359,321.

(30) Foreign Application Priority Data

Dec. 20, 2011 (JP) ................. 2011-277926

(51) Int. Cl.
| | |
|---|---|
| *C07D 405/12* | (2006.01) |
| *A61K 31/341* | (2006.01) |
| *A61K 31/4025* | (2006.01) |
| *A61K 36/8965* | (2006.01) |
| *C07D 307/48* | (2006.01) |
| *C07D 307/50* | (2006.01) |
| *A23L 19/00* | (2016.01) |
| *A23L 33/105* | (2016.01) |

(52) U.S. Cl.
CPC .......... *A61K 31/4025* (2013.01); *A23L 19/09* (2016.08); *A23L 33/105* (2016.08); *A61K 31/341* (2013.01); *A61K 36/8965* (2013.01); *C07D 307/48* (2013.01); *C07D 307/50* (2013.01); *C07D 405/12* (2013.01); *A61K 2236/37* (2013.01); *A61K 2236/39* (2013.01)

(58) Field of Classification Search
None
See application file for complete search history.

(56) References Cited

U.S. PATENT DOCUMENTS 9,359,321 B2 * 6/2016 Nishioka ............ A61K 36/8965

FOREIGN PATENT DOCUMENTS

| | | | |
|---|---|---|---|
| AU | EP 1842536 A1 * | 10/2007 | ............ A61K 31/19 |
| JP | 2006-206489 A | 10/2006 | |
| JP | 2007-045750 A | 2/2007 | |
| JP | 2007-230870 A | 9/2007 | |
| JP | 2008-193933 A | 8/2008 | |
| JP | 2010-248107 A | 11/2010 | |
| JP | 2011-153125 A | 8/2011 | |
| KR | 10-2007-0039409 A | 4/2007 | |

OTHER PUBLICATIONS

Rasmussen, et al., Acta pharmacol. et toxicol., 50:81 (1982), p. 81 only.*
Matzi, et al., European Journal of Cardio-thoracic Surgery, 32:776 (2007).*
Translation of EP1842536A1 by Google Patents, https://www.google.com/patents/EP1842536A1 (2007).*
Dai Yan et al, Cell Stress & Chaperones; 9(4): 378-389 (2004).
Hirata I et al, Digestion; 79(4): 243-50 (2009).
Sarah M. et al, FASEB J. 22: 3836-3845 (2008).
Tadashi Nishida et al, Journal of clinical biochemistry and nutrition; 46(1): 43-51 (2010).
Kiao-Rong Chang et al, World J Gastroenterol; 13(32): 4355-4359 (2007).
Tomohiro Ito et al, New Food Industry, Aug. 1, 2012, vol. 54, No. 8, p. 1-9.

(Continued)

*Primary Examiner* — Michael Barker
(74) *Attorney, Agent, or Firm* — Enshan Hong; VLP Law Group LLP

(57) ABSTRACT

A method for induction of a heat shock protein, anti-stress or regulation of an autonomic nerve comprises: administering a mammalian subject in need thereof a composition comprising an effective amount of hydroxymethylfurfural derivative of the following formula:

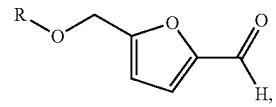

wherein R is selected from the group consisting of formula (I):

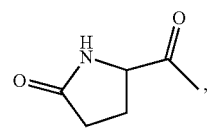

(II): $HOOCCH_2COCO-$, (III): $HOOCCH_2CH_2COCO-$, and (IV): a hydrogen atom.

15 Claims, 15 Drawing Sheets

(56) References Cited

OTHER PUBLICATIONS

USDA Agricultural Information Bulletin No. 539 (2009).
Ruflan-Henares, et al., European Food Research and Technology, 228:249 (208).
Office action issued on Aug. 2, 2016 by the Japan Patent Office for related Japanese Application No. 2013-550324.

* cited by examiner

SEQUENCE LISTING

```
<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: HSP70 forward primer

<400> SEQUENCE: 1
gcatttccta gtatttctgt ttgt                                          24

<210> SEQ ID NO 2
<211> LENGTH: 23
<212> TYPE: DNA
<213> ORGANISM: Artificial Sequence
<220> FEATURE:
<223> OTHER INFORMATION: HSP70 reverse primer

<400> SEQUENCE: 2
aatagtcgta agatggcagt ata                                           23

<210> SEQ ID NO 3
<211> LENGTH: 19
<212> TYPE: DNA
<213> ORGANISM: Artificial Sequence
<220> FEATURE:
<223> OTHER INFORMATION: beta 2 microglobulin forward primer

<400> SEQUENCE: 3
tagctgtgct cgcgctact                                                19

<210> SEQ ID NO 4
<211> LENGTH: 20
<212> TYPE: DNA
<213> ORGANISM: Artificial Sequence
<220> FEATURE:
<223> OTHER INFORMATION: beta 2 microglobulin reverse primer

<400> SEQUENCE: 4
agtgggggtg aattcagtgt                                               20

<210> SEQ ID NO 5
<211> LENGTH: 20
<212> TYPE: DNA
<213> ORGANISM: Artificial Sequence
<220> FEATURE:
<223> OTHER INFORMATION: HSP70 forward primer

<400> SEQUENCE: 5
caagatcacc atcaccaacg                                               20

<210> SEQ ID NO 6
<211> LENGTH: 20
<212> TYPE: DNA
<213> ORGANISM: Artificial Sequence
<220> FEATURE:
<223> OTHER INFORMATION: HSP70 reverse primer

<400> SEQUENCE: 6
ctcaaactcg tccttctcgg                                               20
```

METHOD FOR INDUCTION OF A HEAT SHOCK PROTEIN, ANTI-STRESS OR REGULATION OF AN AUTONOMIC NERVE

CROSS REFERENCE TO RELATED APPLICATIONS

This application is a continuation of U.S. patent application Ser. No. 14/366,276, which entered U.S. national phase on Jun. 18, 2014 from international patent application No. PCT/JP2012/083040, which was filed on Dec. 20, 2012, which claimed priority from Japanese Application No.: 2011-277926 filed on Dec. 20, 2011, the entire content of which is herein incorporated as reference.

SEQUENCE LISTING

The instant application contains a Sequence Listing which has been submitted electronically in ASCII format and is hereby incorporated by reference in its entirety. Said ASCII copy, created on Oct. 24, 2014, is named 12F096-PCT_ST25.txt and is 1,458 bytes in size.

BACKGROUND OF THE INVENTION

1. Field of the Invention

The present disclosure relates to hydroxymethylfurfural derivatives, pharmaceuticals, heat shock protein inducers, anti-stress agents, autonomic nerve regulators, foods and drinks, and methods of producing the hydroxymethylfurfural derivative.

2. Description of the Related Art

People nowadays are exposed to long working hours, various physical and mental stress environment, or the like; and many of those people complain physical symptoms such as loss of appetite, sleep disruption, dizziness, or cold sweat, or mental symptoms such as a hatred or distrust of other people, emotional instability, state of being irritated, or depressed mood, even though no abnormalities are found when examinations such as physical checkup. Symptoms associated with such unidentified complaints are often diagnosed as dysautonomia. In the present circumstances, such a dysautonomia is usually treated with a drug therapy such as a minor tranquilizer or hormonal agent, treatment by diet, lifestyle changes for the better such as exercise, or the like.

It has been known that autonomic disorders including dysautonomia described above are induced by excessive loads of stress. In the autonomic disorder, disturbance in the balance between the sympathetic nerve and the parasympathetic nerve (the balance of the autonomic nerve), lowered activity of the autonomic nerve, or the like is observed. The disturbance in the balance of the autonomic nerve means a state with increased activity of the sympathetic nerve or a state with increased activity of the parasympathetic nerve. Further, it has been known that the capacity to deal with stress is decreased by a lowered activity of the autonomic nerve. For instance, because functions of the gastrointestinal tract are mainly innervated by the parasympathetic nerve, prolonged tonus of the sympathetic nerve due to loads of stress suppresses the function of the gastrointestinal tract, resulting in gastrointestinal disorders such as loss of appetite or constipation. In addition, it is thought that when the parasympathetic nerve does not function well because of loads of stress and the activity of the sympathetic nerve remains elevated, sleep disruption is brought about.

While there is, as described above, a close relationship between stresses and autonomic disorders, there are also autonomic disorders that are not caused by loads of stress. In addition, the load of stress does not necessarily bring about the autonomic disorder and may in some cases induce other physical symptoms.

As one of the proteins called stress proteins, there are heat shock proteins (hereinafter, referred to as HSPs). HSPs are proteins with a molecular weight of about several tens of thousands to one hundred fifty thousand and are divided into several families on the basis of the molecular weight thereof (HSP10, HSP27, HSP40, HSP60, HSP70, HSP90, HSP110, and the like). HSPs are a group of proteins that are induced within cells when living organisms are put under physical, chemical, physiological, or mental stress. To be specific, HSPs have a role of protecting cells, exhibiting increased expression when living organism are exposed to various conditions including heat, bacterial infection, inflammation, reactive oxygen species, ultraviolet rays, starvation, and hypoxia. In addition, HSPs also have functions as molecular chaperones including control of protein folding and inhibition of aggregation of abnormal proteins.

Among HSPs, HSP70 has been actively studied in particular, and has been reported to be constitutively expressed in many internal organs including the gastrointestinal tract and skin. Recently, HSP70's antiapoptotic action and anti-inflammatory action have been recognized and HSP70's cell protection effect against various stresses has been reported (Non Patent Literatures 1 to 4). Due to this, studies have come to be conducted, attempting to apply materials with HSP70 inducing activities in pharmaceuticals, cosmetics, or the like. When it comes to natural product-derived materials with the HSP70 inducing activity, paeoniflorin which is a major component of *Paeoniae radix* has been reported (Non Patent Literature 5).

Asparagus is a vegetable that is cultivated and harvested in various regions including Hokkaido in Japan. It has been found that asparagus has various biological activities. Patent Literature 1 describes that an asparagus stem extract has preventive and restorative effects for various types of fatigue (such as physical fatigue or fatigue due to mental stress). Further, Patent Literature 2 describes that an asparagus stem extract has an effect of improving brain functions. Further, Patent Literature 3 describes that an asparagus pseudo leaf extract has an effect of controlling the autonomic nerve.

CITED LITERATURE

Patent Literature

Patent Literature 1: Unexamined Japanese Patent Application Kokai Publication No. 2007-45750
Patent Literature 2: Unexamined Japanese Patent Application Kokai Publication No. 2007-230870
Patent Literature 3: Unexamined Japanese Patent Application Kokai Publication No. 2011-153125

Non Patent Literature

Non Patent Literature 1: Xiao-Rong Chang et al, World J Gastroenterol; 13(32):4355-4359 (2007)
Non Patent Literature 2: Sarah M. et al, FASEB J. 22, 3836-3845 (2008)
Non Patent Literature 3: Hirata I et al, Digestion; 79(4):243-50 (2009)
Non Patent Literature 4: Tadashi Nishida et al, Journal of clinical biochemistry and nutrition; 46(1):43-51 (2010)

Non Patent Literature 5: Dai Yan et al, Cell Stress & Chaperones; 9(4), 378-389 (2004)

SUMMARY OF THE INVENTION

However, there has thus far been no report concerning components in asparagus extracts or products obtained by processing asparagus, which components are involved in an anti-stress effect and autonomic nerve regulatory effect.

The present inventors discovered a novel hydroxymethylfurfural derivative that was derived from a product obtained by heat-treating asparagus with hot water, and found out that such a hydroxymethylfurfural derivative has an excellent HSP inducing activity, anti-stress effect, and autonomic nerve regulatory effect, thereby completing the present disclosure. An objective of the disclosure is to provide a novel hydroxymethylfurfural derivative, a highly effective pharmaceutical, HSP inducer, anti-stress agent, and autonomic nerve regulator. Further, it is an objective to provide foods and drinks having an excellent HSP inducing activity, anti-stress effect, and autonomic nerve regulatory effect. Further, it is an objective to provide a method of producing a hydroxymethylfurfural derivative that can reduce the cost and is simple and convenient.

In order to attain the above object, a hydroxymethylfurfural derivative in accordance with a first viewpoint of the present disclosure is represented by the general formula

[FORMULA 1]

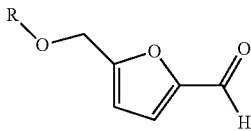

(wherein, R is selected from the group consisting of the following formula (I),

[FORMULA 2]

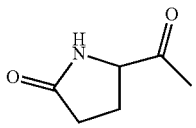

(II) HOOCCH$_2$COCO—, (III) HOOCCH$_2$CH$_2$COCO—, and (IV) a hydrogen atom).

The above-mentioned hydroxymethylfurfural derivative may be obtained by heat-treating an asparagus stem with hot water.

A pharmaceutical in accordance with a second viewpoint of the present disclosure has the above-mentioned hydroxymethylfurfural derivative as an active component.

A heat shock protein inducer in accordance with a third viewpoint of the present disclosure has the above-mentioned hydroxymethylfurfural derivative as an active component.

An anti-stress agent in accordance with a fourth viewpoint of the present disclosure has the above-mentioned hydroxymethylfurfural derivative as an active component.

An autonomic nerve regulator in accordance with a fifth viewpoint of the present disclosure has the above-mentioned hydroxymethylfurfural derivative as an active component.

A food or drink in accordance with a sixth viewpoint of the present disclosure is characterized by comprising the above-mentioned heat shock protein inducer, the above-mentioned anti-stress agent, or the above-mentioned autonomic nerve regulator.

A method of producing a hydroxymethylfurfural derivative in accordance with a seventh viewpoint of the present disclosure comprises the step of heat-treating an asparagus stem with hot water.

The above-mentioned method of production may comprise the step of an enzyme treatment.

A heat shock protein inducer in accordance with an eighth viewpoint of the present disclosure has a product obtained by heat-treating an asparagus stem with hot water as an active component.

An anti-stress agent in accordance with a ninth viewpoint of the present disclosure has a product obtained by heat-treating an asparagus stem with hot water as an active component.

An autonomic nerve regulator in accordance with a tenth viewpoint of the present disclosure has a product obtained by heat-treating an asparagus stem with hot water as an active component.

According to the present disclosure, a novel hydroxymethylfurfural derivative, a highly effective pharmaceutical, HSP inducer, anti-stress agent, and autonomic nerve regulator can be provided. In addition, foods and drinks having an excellent HSP inducing activity, anti-stress effect, and autonomic nerve regulatory effect can be provided. Further, a method of producing a hydroxymethylfurfural derivative that can reduce the cost and is simple and convenient can be provided.

DETAILED DESCRIPTION OF THE PRESENTLY PREFERRED EMBODIMENTS

Figure 1:
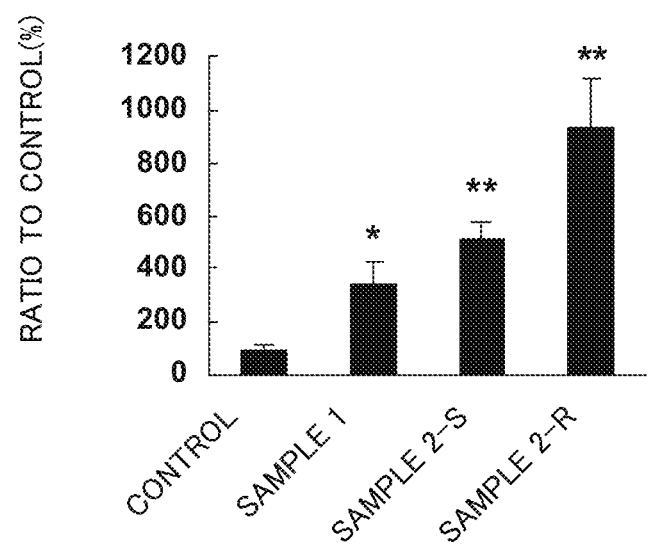
FIG. 1 is a figure showing the HSP70 mRNA expression inducing activity by a hydroxymethylfurfural derivative.

Embodiments of the present disclosure will be described in detail below.

(1. Hydroxymethylfurfural Derivative)

The hydroxymethylfurfural derivative according to the present disclosure is represented by the following general formula.

[FORMULA 3]

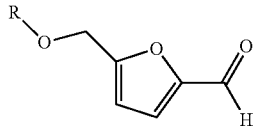

In the above general formula, R selected from the group consisting of the following formula (I),

[FORMULA 4]

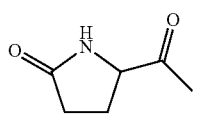
(I)

(II) $HOOCCH_2COCO-$, and (III) $HOOCCH_2CH_2COCO-$, and (IV) a hydrogen atom.

In cases where R is the above formula (I), the hydroxymethylfurfural derivative is represented by the following structural formula.

[FORMULA 5]

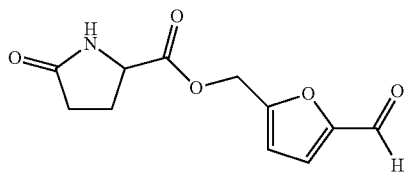

In cases where R is the above formula (I), the hydroxymethylfurfural derivative includes the following two stereo isomers (R form and S form).

[FORMULA 6]

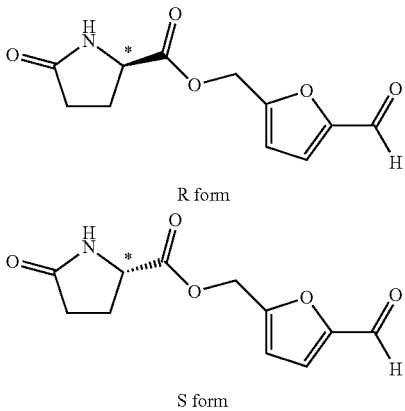

R form

S form

In cases where R is the above (IV) a hydrogen atom, the hydroxymethylfurfural derivative is represented by the following structural formula (name of compound: hydroxymethylfurfural).

[FORMULA 7]

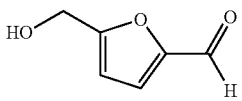

The hydroxymethylfurfural derivative according to the present disclosure may be, as shown below, obtained by heat-treating an asparagus stem with hot water.

The hydroxymethylfurfural derivative according to the present disclosure, as shown below, has an excellent heat shock protein inducing activity, anti-stress effect, and autonomic nerve regulatory effect.

(2. Method of Producing a Hydroxymethylfurfural Derivative)

The method of producing a hydroxymethylfurfural derivative according to the present disclosure comprises the step of heat-treating an asparagus stem with hot water.

In the present specification, the phrase "heat-treating with hot water" means heat-treating in hot water. As an asparagus stem used in the present disclosure, the stem portion of, for example, green asparagus, white asparagus, purple asparagus, or the like can be used. Further, the origin of asparagus is not particularly restricted; and asparagus that is domestically produced may be used or asparagus that is imported may be used. As long as asparagus is one that brings out effects of the present disclosure, asparagus may be selected as appropriate.

The step of heat-treating an asparagus stem with hot water is carried out by, for example, adding 1 to 50 volumes of water to an asparagus stem and heating in hot water for 20 to 180 minutes. A temperature on this occasion is, preferably, 50 to 300° C. In cases where the heat treatment is carried out under atmospheric pressure, it is preferred to be, for example, a temperature of 100° C., or more. It is to be noted that the heat treatment with hot water may be carried out under pressure being applied and the pressure is preferably, for example, 0.1 to 0.2 MPa (for example, 0.12 MPa in cases where an autoclave is used).

As described above, the hydroxymethylfurfural derivative according to the present disclosure is obtained by heat-treating an asparagus stem with hot water. Thus, the method of producing a hydroxymethylfurfural derivative according to the present disclosure comprises the step of heat-treating an asparagus stem with hot water. In such a method of production, because the stem portion of asparagus which is widely distributed as a vegetable is used, the hydroxymethylfurfural derivative can be produced at low cost. In addition, the hydroxymethylfurfural derivative can be simply and conveniently produced by heat-treating asparagus with hot water without using sophisticated techniques, special devices, or the like. Further, because asparagus which is a food material is subjected to the heat treatment with hot water, the hydroxymethylfurfural derivative obtained by such a method of production can be said to be high in safety; and the asparagus stem can be sterilized because of heating with hot water. It is to be noted that as long as a method of heat treatment with hot water is one that brings out effects of the present disclosure, the method may be selected as appropriate.

For the purpose of increasing the efficiency of the step of heat treatment with hot water to efficiently produce hydroxymethylfurfural derivatives, the method of producing a hydroxymethylfurfural derivative according to the present disclosure may comprise additional steps illustrated below.

Examples of the above additional step may include the step of finely chopping asparagus stems before the heat treatment with hot water. The asparagus stem can finely chopped into pieces of about 0.5 to 10 cm in size. The fine chopping may be manually carried out using, for example, a knife, cutter, or the like. Or a machine such as a chopping machine or mill may be used. As long as a method of finely chopping is one that brings out effects of the present disclosure, the method may be selected as appropriate.

Examples of the above additional step may include the step of compressing asparagus stems before the heat treatment with hot water. The asparagus stem can be compressed using, for example, a compressor. As long as a method of compressing is one that brings out effects of the present disclosure, the method may be selected as appropriate.

Examples of the above additional step include, for the purpose of breaking down plant tissues or the like, the step of an enzyme treatment before or after the step of the heat treatment with hot water. The enzyme treatment increases the efficiency of the step of the heat treatment with hot water, which allows hydroxymethylfurfural derivatives to be more efficiently produced. For instance, an enzyme such as cellulase, hemicellulase, pectinase, amylase, or pullulanase; or a combination of 2, 3, or more of these enzymes is suitably used for the purpose of efficiently breaking down fibers, pectin, or the like in the asparagus stem. As long as an enzyme is one that brings out effects of the present disclosure, the enzyme may be selected as appropriate. In the step of the enzyme treatment, an amount to be added, temperature, and reaction time that are most appropriate for the enzyme to be used may be selected. In cases where cellulase is used, the enzyme treatment can be carried out, for example, at an amount of cellulase added of 0.1 to 5% (w/w) at a temperature of 30 to 60° C., for 1 to 72 hours. The step of the enzyme treatment may be carried out before the step of the heat treatment with hot water or may be after the step of the heat treatment with hot water. It is to be noted that, from the viewpoint of efficiently breaking down cellulose in the asparagus stem to more efficiently produce the hydroxymethylfurfural derivative, it is preferred to carry out the enzyme treatment by cellulase after the step of the heat treatment with hot water. As long as a method of enzyme treatment is one that brings out effects of the present disclosure, the method may be selected as appropriate.

Examples of the above additional step include the step of mechanically grinding residues after the heat treatment with hot water. In the grinding, a machine such as a mill or blender may, for example, be used. As long as a method of grinding is one that brings out effects of the present disclosure, the method may be selected as appropriate.

Examples of the above additional step include the step of centrifugation or filtration after the heat treatment with hot water. Further inclusion of these steps enables the residue to be efficiently removed to obtain a heat treatment liquid. The centrifugation may be carried out, for example, at a revolution of 3,000 to 7,000 rpm at 4 to 50° C. In the filtration, a commercially available filter paper, filter cloth, or the like may, for example, be used. As long as a method of centrifugation or a method of filtration is one that brings out effects of the present disclosure, the method may be selected as appropriate.

Examples of the above additional step include the step of concentrating the obtained heat treatment liquid under reduced pressure after the heat treatment with hot water. The concentration can be carried out, for example, by an evaporator or the like. As long as a method of concentration is one that brings out effects of the present disclosure, the method may be selected as appropriate.

Examples of the above additional step include the step of spray drying or freeze drying the heat treatment liquid after the heat treatment with hot water. The spray drying may be carried out, for example, at an exhaust air temperature of 70 to 90° C., and a chamber temperature of 80 to 100° C. As long as a method of spray drying or a method of freeze drying is one that brings out effects of the present disclosure, the method may be selected as appropriate.

By further including the additional step illustrated above in the step of heat-treating an asparagus stem with hot water, the hydroxymethylfurfural derivative can be more efficiently produced. As long as an additional step is one that brings out effects of the present disclosure, the step may be selected as appropriate.

The step of heat-treating an asparagus stem with hot water will be illustrated below. The asparagus stem is finely chopped into pieces of about 0.5 to 10 cm and added with 1 to 50 volumes of water. The heat treatment with hot water is carried out at 50 to 100° C., or at 121° C. under pressure being applied, for 20 to 180 minutes. The resultant was, after allowed to cool, added with cellulase at 0.1 to 5% (w/w); and enzyme treatment is carried out at 30 to 60° C., for 1 to 72 hours. Subsequently, residues are then mechanically ground and centrifuged at a revolution of 3,000 to 7,000 rpm at 4 to 50° C., to obtain a supernatant. Such a supernatant is then subjected to spray drying at an exhaust air temperature of 70 to 90° C., and a chamber temperature of 80 to 100° C.

In the present specification, a "product obtained by heat-treating an asparagus stem with hot water" refers to one obtained by heat-treating an asparagus stem in hot water, and then removing residues by centrifugation, filtration, or the like, followed by concentration. Further, in the present specification, a "product obtained by heat-treating an asparagus stem with hot water and an enzyme treatment" means a product obtained by heat-treating an asparagus stem with hot water that is obtained by going through the step of the enzyme treatment as described above before or after the step of the heat treatment with hot water. In the product obtained by heat-treating an asparagus stem with hot water and the product obtained by heat-treating an asparagus stem with hot water and enzyme treatment, the aforementioned hydroxymethylfurfural derivative is contained, for example, at least 0.05% or more as an active component.

The obtained hydroxymethylfurfural derivative by the method of production according to the present disclosure can be fractionated by, for example, dissolving the product obtained by heat-treating an asparagus stem with hot water in water or an organic solvent (such as methanol) and subjecting to open column chromatography with a reverse phase carrier (for example, DIAION HP-20 (product name) (manufactured by Mitsubishi Chemical Corporation) or the like). It also can, for example, be fractionated by a carrier for gel filtration (for example, Sephadex LH-20 (product name) (manufactured by Pharmacia Fine Chemicals) or the like). Further, a predetermined fraction that is eluted by the above-mentioned method can be purified, for example, by isolating by high performance liquid chromatography (HPLC).

Without wishing to be bound by a particular theory, it is thought that, by heat-treating the asparagus stem with hot water as described above, an organic acid and sugars derived from the asparagus stem are reacted at high temperatures, thereby obtaining the hydroxymethylfurfural derivative according to the present disclosure. Examples of the organic acid include pyroglutamic acid, α-ketoglutaric acid, and oxaloacetic acid. Meanwhile, examples of the sugar include fructose, glucose, sucrose, or mannose.

For instance, it is thought that, in the step of heat-treating an asparagus stem with hot water, pyroglutamic acid and fructose which are derived from the asparagus stem are reacted at high temperatures, thereby obtaining the following compound.

[FORMULA 8]

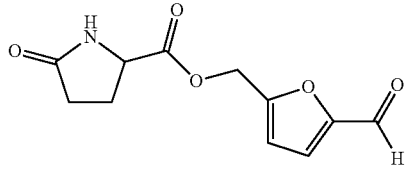

In the method of producing a hydroxymethylfurfural derivative according to the present disclosure, plants other than asparagus, the plant containing an organic acid and sugar illustrated above, can be used as appropriate. Vegetables that contain pyroglutamic acid and fructose can, for example, preferably be used. Vegetables such as cabbage, broccoli, pumpkin, onion, garlic, or carrot may, for example, be suitably used. As long as a plant is one that brings out effects of the present disclosure, the plant may be selected as appropriate.

(3. HSP Inducer, Anti-Stress Agent, and Autonomic Nerve Regulator)

By the present disclosure, an HSP inducer, anti-stress agent, and autonomic nerve regulator that contain the hydroxymethylfurfural derivative according to the present disclosure as an active component are provided.

The HSP inducer according to the present disclosure may be used in order to induce HSP that is present in vivo or in vitro. HSP used here is, for example, HSP70, HSP10, HSP27, HSP40, HSP60, HSP90, HSP110, or the like, with HSP70 being preferred. An HSP inducing activity can be evaluated, for example, by culturing cells with such a HSP inducer being added and measuring, by a known method, an HSP mRNA expression inducing activity, HSP protein expression inducing activity, or the like. As long as a method of evaluation is one that brings out effects of the present disclosure, the method may be selected as appropriate.

The anti-stress agent according to the present disclosure can be administered to a living organism to thereby obtain an anti-stress effect. The anti-stress effect can be evaluated, for example, by administrating such an anti-stress agent to mammals and measuring an oxidative stress index, stress hormone concentration in the blood, or the like before and after the administration. As long as a method of evaluation is one that brings out effects of the present disclosure, the method may be selected as appropriate.

The autonomic nerve regulator according to the present disclosure can be administered to living organisms to thereby obtain an autonomic nerve regulatory effect. The autonomic nerve regulatory effect can be evaluated, for example, by administrating such an autonomic nerve regulator to mammals and measuring an autonomic nervous balance, an autonomic nervous activity, or the like before and after the administration. As long as it is a method of evaluation is one that brings out effects of the present disclosure, the method may be selected as appropriate.

Further, by the present disclosure, an HSP inducer, anti-stress agent, and autonomic nerve regulator that contain a product obtained by heat-treating an asparagus stem with hot water as an active component are also provided. Such a product obtained by heat-treating an asparagus stem with hot water is, as described above, obtained by heat-treating an asparagus stem with hot water. Therefore, the hydroxymethylfurfural derivative according to the present disclosure is contained in such a product obtained by heat-treating an asparagus stem with hot water.

(4. Foods and Drinks, and Pharmaceuticals)

By the present disclosure, foods and drinks that contain the HSP inducer, anti-stress agent, and autonomic nerve regulator according to the present disclosure are provided. Such foods and drinks can be processed, by a conventional method, into a form suitable to eat and drink including, for example, a form of granule, a form of particulate, tablets, capsules, a form of gel, a form of cream, a form of paste, a form of suspension, a form of aqueous solution, a form of emulsion, and a form of powder. In addition, excipients, binders, lubricants, coloring agents, disintegrants, thickeners, preservatives, stabilizers, pH adjusters, or the like, which are usually used in foods and drinks, can be added. Further, for the purpose of improving the quality of taste, sugars, sugar alcohols, salts, fats and oils, amino acids, organic acids, glycerin, or the like can be added in a range where the effects of the present disclosure is not impaired. It is to be noted that in cases where the HSP inducer, anti-stress agent, and autonomic nerve regulator according to the present disclosure are added to existing foods and drinks and used, any foods and drinks may be selected as appropriate as base foods and drinks as long as the foods and drinks are ones that bring out effects of the present disclosure.

In cases where the HSP inducer, anti-stress agent, and autonomic nerve regulator according to the present disclosure are used as a food or drink, the food or drink can be taken at, for example, 50 mg to 2000 mg/day, and preferably 100 mg to 1000 mg/day, in terms of a product obtained by heat-treating an asparagus stem with hot water (or a product obtained by heat-treating an asparagus stem with hot water and enzyme treatment) to thereby obtain a desired HSP inducing activity, anti-stress effect, and autonomic nerve regulatory effect. The intake amount taken may be selected as appropriate on the basis of an object of intake, a form of food or drink, or the like.

The foods and drinks according to the present disclosure have both an anti-stress effect and autonomic nerve regulatory effect. Therefore, it is expected that the anti-stress effect and autonomic nerve regulatory effect synergistically act to bring out a higher effect on autonomic disorders by loads of stress. In addition, it is expected to bring out an autonomic nerve regulatory effect also for autonomic disorders that are not caused by loads of stress.

The HSP inducer, anti-stress agent, and autonomic nerve regulator according to the present disclosure can be used as a pharmaceutical. The pharmaceutical according to the present disclosure contains the aforementioned hydroxymethylfurfural derivative as an active component. In this case, the pharmaceutical can be prepared, by a conventional method, in a dosage form including, for example, tablets, granules, powders, capsules, syrups, and injection solutions. Further, excipients, binders, lubricants, coloring agents, disintegrants, thickeners, preservatives, stabilizers, pH adjusters, or the like, which are usually used in pharmaceuticals, can be added. A method of administration may be selected as appropriate in a range where effects of the present disclosure is brought out, which method includes oral administration, intravenous administration, intraperitoneal administration, intradermal administration, and sublingual administration.

In cases where the HSP inducer, anti-stress agent, and autonomic nerve regulator according to the present disclosure are used as a pharmaceutical, the pharmaceutical can be administrated at, for example, 50 mg to 2000 mg/day, and preferably 100 mg to 1000 mg/day, in terms of a product obtained by heat-treating an asparagus stem with hot water (or a product obtained by heat-treating an asparagus stem with hot water and enzyme treatment) to thereby obtain a desired HSP inducing activity, anti-stress effect, and autonomic nerve regulatory effect. The dosage may be selected as appropriate on the basis of an object of administration, dosage form, patients' age and body weight, or the like.

EXAMPLES

By way of the examples, the present disclosure will be concretely described below. However, the present disclosure is by no means limited to these examples.

Example 1

Production of Hydroxymethylfurfural by Heat-Treating an Asparagus Stem with Hot Water Water 1.5 L was added to green asparagus stem (fresh weight 1.5 kg); and the mixture was, for the purpose of heat treatment with hot water, autoclaved (121° C., for 20 minutes) using an autoclave and filtered with a filter cloth. The obtained liquid was concentrated under reduced pressure in an evaporator to obtain a heat treatment product. The obtained heat treatment product was fractionated by column chromatography (product name: DIAION HP-20, manufactured by Mitsubishi Chemical Corporation; 500 mL, elution; $H_2O$, 50% methanol, 100% methanol) to obtain 1.7 g. Next, the obtained fractionation product was purified by preparative HPLC (product name: Hitachi L-7100, manufactured by Hitachi Ltd.) to obtain the compound (X) (5.0 mg). A column whose product name: CAPCELL PAK C18 UG 120, 20φ×250 mm (manufactured by Shiseido Co., Ltd.) was used; and the mobile phase was as shown in Table 1 (A: $H_2O$, B: methanol). The flow rate of preparative HPLC was 8 mL/min and detection was carried out at a detection wavelength of 280 nm by an ultraviolet absorbance detector.

TABLE 1

| Time (minutes) | A(%) | B(%) |
|---|---|---|
| 0 | 80 | 20 |
| 10 | 80 | 20 |
| 30 | 50 | 50 |
| 40 | 50 | 50 |
| 41 | 80 | 20 |
| 45 | 80 | 20 |

The NMR data of the compound (X) obtained as described above are shown below.

$^1$H-NMR (400 MHz, DMSO-$d_6$)
δ 4.49 (1H, dd, J=5.2 Hz)
5.59 (1H, dt, J=5.6 Hz)
6.55 (1H, d, J=3.6 Hz)
7.48 (1H, d, J=3.6 Hz)
9.52 (1H, s)
$^{13}$C-NMR (100 MHz, DMSO-$d_6$)
δ 55.9
109.7
124.5
151.7
162.1
178.0

In order to determine the structure of the compound (X) obtained above, the NMR data of a commercially available product of hydroxymethylfurfural (product name: 5-Hydroxymethyl-2-furaldehyde, Tokyo Chemical Hanbai Co., Ltd.) was compared with that of the compound (X). The NMR data of the commercially available product of hydroxymethylfurfural is shown below.

$^1$H-NMR (400 MHz, DMSO-$d_6$)
δ 5.51 (1H, dd, J=5.2 Hz)
5.59 (1H, dt, J=5.6 Hz)
6.60 (1H, d, J=3.6 Hz)
7.49 (1H, d, J=3.6 Hz)
9.56 (1H, s)
$^{13}$C-NMR (100 MHz, DMSO-$d_6$)
δ55.9
109.7
124.4
151.7
162.1
177.9

Because the NMR data of the compound (X) obtained above matched that of the commercially available product, it was proven that the compound (X) was hydroxymethylfurfural (the following structural formula). From the above, it became apparent that hydroxymethylfurfural was contained in the product obtained by heat-treating an asparagus stem with hot water.

[FORMULA 9]

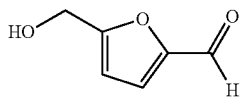

Example 2

Production of Novel Hydroxymethylfurfural Derivative by Heat-Treating an Asparagus Stem with Hot Water Water 1 L was added to green asparagus stem (fresh weight 1.0 kg); and the mixture was, for the purpose of heat treatment with hot water, autoclaved (121° C., for 20 minutes) using an autoclave and filtered with a filter cloth. The obtained liquid was concentrated under reduced pressure in an evaporator to obtain a product obtained by heat-treating an asparagus stem with hot water. The obtained heat treatment product was fractionated by column chromatography (product name: DIAION HP-20, manufactured by Mitsubishi Chemical Corporation; 500 mL, elution; $H_2O$, 30% methanol, 100% methanol). Next, the obtained fractionation product 723.8 mg was purified by column chromatography (product name: Sephadex LH-20, manufactured by Pharmacia Fine Chemicals; 250 mL, elution; $H_2O$). Further, the obtained fractionation product 12.6 mg was purified by preparative HPLC (product name: Hitachi L-7100, manufactured by Hitachi Ltd.) to obtain the compound (Y) (2.0 mg). The conditions for the preparative HPLC were the same as those in Example 1.

The compound (Y) obtained above was subjected to HPLC analysis (product name: Hitachi L-7100, manufactured by Hitachi Ltd.) and, as a result, the retention time was found to be 22.99 minutes. In this analytical HPLC, a column whose product name: CAPCELL PAK C18 UG 120, 4.6ϕ×250 mm (manufactured by Shiseido Co., Ltd.) was used; and the mobile phase was as shown in Table 2 (C: 20 mM sodium phosphate buffer (pH 2.3), D: acetonitrile). The flow rate of analytical HPLC was 1 mL/min and detection was carried out at a detection wavelength of 280 nm by an ultraviolet absorbance detector.

TABLE 2

| Time (minutes) | C(%) | D(%) |
|---|---|---|
| 0 | 95 | 5 |
| 5 | 95 | 5 |
| 20 | 90 | 10 |
| 25 | 90 | 10 |
| 30 | 50 | 50 |
| 35 | 50 | 50 |
| 36 | 95 | 5 |

The LC/Tof MS analysis data of the compound (Y) obtained above are shown below.

Found m/z 238.0710 ([M+H]+); $C_{11}H_{12}NO_5$

Theoretical value m/z 238.0715 ([M+H]+); $C_{11}H_{12}NO_5$

From the above, it became apparent that the compound (Y) obtained above has a molecular formula of $C_{11}H_{11}NO_5$.

The $^1$H-NMR data of the compound (Y) obtained above are shown below.

$^1$H-NMR (400 MHz, $CD_3OD$)

δ 2.00 (4H, m)

4.20 (1H, dd, J=3.9, 9.2 Hz)

5.20 (2H, s)

6.55 (1H, d, J=3.6 Hz)

7.37 (1H, d, J=3.6 Hz)

9.45 (1H, s)

Example 3

Synthesis of Novel Hydroxymethylfurfural Derivative

It was estimated that the compound (Y) ($C_{11}H_{11}NO_5$) obtained in Example 2 was generated by reacting pyroglutamic acid ($C_5H_7NO_3$) and fructose ($C_6H_{12}O_6$) derived from the asparagus stem under heating. In order to verify this, a compound was synthesized by the following method using pyroglutamic acid and fructose. It is to be noted that because stereo isomers were, as described below, thought to exist for the compound (Y), an S(L) form and R(D) form were synthesized with L-pyroglutamic acid as a starting material and with D-pyroglutamic acid as a starting material, respectively.

[FORMULA 10]

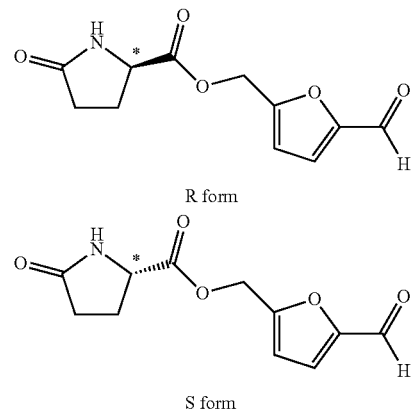

R form

S form

L-pyroglutamic acid (product name: L-pyroglutamic acid, Tokyo Chemical Hanbai Co., Ltd.) 3.0 g and D-fructose (product name: D(−)-fructose, Junsei Chemical Co., Ltd.) 1.5 g were mixed in an Erlenmeyer flask and autoclaved (121° C., for 20 minutes) using an autoclave. The obtained reaction product was fractionated by column chromatography (product name: DIAION HP-20, manufactured by Mitsubishi Chemical Corporation; 150 mL, elution; $H_2O$, 30% methanol, 100% methanol). Further, a 100% methanol fraction was purified by preparative HPLC using a column (product name: CAPCELL PAK C18 UG 120, 20ϕ×250 mm, manufactured by Shiseido Co., Ltd.) to obtain S form compound (Z) (24.4 mg). The conditions for the preparative HPLC were the same as those in Example 1.

D-pyroglutamic acid (product name: D-pyroglutamic acid, Tokyo Chemical Hanbai Co., Ltd.) 2.0 g and D-fructose (product name: D(−)-fructose, Junsei Chemical Co., Ltd.) 1.0 g were mixed in an Erlenmeyer flask and autoclaved (121° C., for 20 minutes) using an autoclave. The obtained reaction product was fractionated by column chromatography (product name: DIAION HP-20, manufactured by Mitsubishi Chemical Corporation; 100 mL, elution; $H_2O$, 30% methanol, 60% methanol). A 60% methanol fraction was concentrated to about 50 mL under reduced pressure by an evaporator and then separated with ethyl acetate (50 mL×5). An ethyl acetate layer was concentrated under reduced pressure by an evaporator and fractionated by column chromatography (product name: DIAION HP-20, manufactured by Mitsubishi Chemical Corporation; 10 mL, elution; $H_2O$, 30% methanol, 60% methanol). A 60% methanol fraction was concentrated under reduced pressure by an evaporator to obtain R form compound (Z) (24.6 mg).

The S form and R form compounds (Z) obtained above were subjected to HPLC analysis (product name: Hitachi L-7100, manufactured by Hitachi Ltd.) and, as a result, the retention time was found to be 22.89 minutes for each. The conditions for the analytical HPLC were the same as those in Example 2.

With regard to the S form and R form compounds (Z) obtained above, MS data and NMR analysis data are shown below.

EI-MS: m/z 237
EI-HR-MS: m/z 237.0612; $C_{11}H_{11}NO_5$
$^1$H-NMR (400 MHz, $CD_3OD$): S form
δ 2.33 (4H, m)
4.34 (1H, dd, J=3.9, 9.0 Hz)
5.51 (2H, s)
6.73 (1H, d, J=3.4 Hz)
7.38 (1H, d, J=3.4 Hz)
9.57 (1H, s)
$^{13}$C-NMR (100 MHz, $CD_3OD$): S form
δ 25.8
30.2
57.0
59.6
114.0
124.0
154.5
156.7
173.4
179.6
181.1
$^1$H-NMR (400 MHz, $CD_3OD$): R form
δ 2.33 (4H, m)
4.34 (1H, dd, J=3.9, 9.0 Hz)
5.27 (2H, s)
6.73 (1H, d, J=3.6 Hz)
7.38 (1H, d, J=3.6 Hz)
9.57 (1H, s)
$^{13}$C-NMR (100 MHz, $CD_3OD$): R form
δ 25.8
30.3
57.0
59.6
113.7
124.0
154.5
156.8
173.4
179.6
181.1

In order to determine the absolute structure of the compound (Y) obtained in Example 2, the compound (Y) obtained in Example 2, the S form compound (Z) and R form compound (Z), both of which were obtained above, were subjected to HPLC analysis (product name: Hitachi L-7100, manufactured by Hitachi Ltd.) using a chiral column (product name: CHIRAL PAK IA, 4.6φ×150 mm, manufactured by Daicel Corporation). The conditions for the analytical HPLC were the same as those in Example 2 except that the different column was used. As a result, the retention time of the S form compound (Z) was found to be 18.92 minutes and the retention time of the R form compound (Z) was found to be 20.57 minutes. Because the retention time of the compound (Y) obtained in Example 2 was 19.06 minutes, it became apparent that the compound (Y) obtained in Example 2 was the S form.

When the HPLC analysis data, LC/Tof MS analysis data, and $^1$H-NMR data in Example 2 were compared with the above-mentioned analysis data in this Example, the compound (Y) obtained by Example 2 and the compound (Z) obtained by this Example were shown to be identical compounds. Therefore, it became apparent that the product obtained by heat-treating an asparagus stem with hot water, which product was obtained in Example 2, at least contained the S form of hydroxymethylfurfural derivative having the following structural formula:

[FORMULA 11]

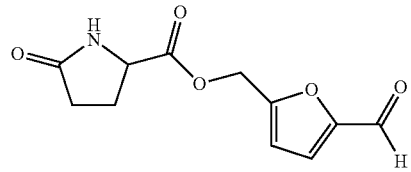

Example 4

Evaluation of HSP70 mRNA Expression Inducing Activity

With regard to a commercially available product of hydroxymethylfurfural (the same as in Example 1) (hereinafter, referred to as sample 1), the S form of hydroxymethylfurfural derivative synthesized in Example 3 (hereinafter, referred to as sample 2-S), and the R form of hydroxymethylfurfural derivative synthesized in Example 3 (hereinafter, referred to as sample 2-R), and a product obtained by heat-treating an asparagus stem with hot water, which product was produced by the following method, (hereinafter, referred to as sample 3), and a product obtained by heat-treating an asparagus stem with hot water and enzyme treatment (hereinafter, referred to as sample 4), an HSP70 inducing activity was evaluated by measuring the mRNA expression level of HSP70.

A method of producing sample 3 is shown below. To green asparagus stems (fresh weight 6.63 kg), water 28.5 L was added; and the mixture was, for the purpose of heat treatment with hot water, autoclaved (121° C., 20 minutes). After cooling, filtration was carried out with a filter paper (product name: Toyo Roshi No. 5A, manufactured by Toyo Roshi Kaisha, Ltd.); and concentration was carried out by an evaporator. To about 10 L of the concentrated liquid, an excipient (product name: Pinedex, manufactured by Matsutani Chemical Industry Co., Ltd.) 275.4 g was added and the resulting mixture was freeze-dried to obtain 542.4 g of powder containing a product obtained by heat-treating an asparagus stem with hot water (in this, the product obtained by heat-treating an asparagus stem with hot water derived from the solid content of asparagus stem accounted for 267.0 g and the excipient accounted for 275.4 g).

A method of producing sample 4 is shown below. To green asparagus stems (fresh weight 12 kg), water 24 L was added; and the mixture was, for the purpose of heat treatment with hot water, autoclaved (121° C., 20 minutes). After allowed to cool to 45° C., the resultant was added with sucrase C (product name) (manufactured by Mitsubishi-Kagaku Foods Corporation) 20 g and Macerozyme A (product name) (manufactured by Yakult Pharmaceutical Industry Co., Ltd.) 20 g; and enzyme treatment was carried out at 45°

C., for three days. Subsequently, autoclave (121° C., 20 minutes) was carried out and filtration was carried out with a filter cloth to collect a filtrate 35 L. Concentration was carried out by an evaporator until the volume reached 9 L. To this concentrated liquid, an excipient (product name: Pinedex, manufactured by Matsutani Chemical Industry Co., Ltd.) 1.20 kg was added; and the resulting mixture was again autoclaved (121° C., 20 minutes). Subsequently, freeze drying was carried out to obtain 2.12 kg of a powder containing a product obtained by heat-treating an asparagus stem with hot water and enzyme treatment (in this, the product obtained by heat-treating an asparagus stem with hot water and enzyme treatment derived from the solid content of asparagus stem accounted for 0.92 kg and the excipient accounted for 1.20 kg).

First, with regard to the sample 1, sample 2-S, and sample 2-R, an HSP70 mRNA expression level was evaluated using human promyelocytic leukemia cells (HL-60 cells).

A method of evaluating the HSP70 mRNA expression level using human promyelocytic leukemia cells (HL-60 cells) is shown below. HL-60 (source: Dainippon Pharmaceutical Co., Ltd.) was suspended in RPMI1640 medium (product name: RPMI1640 medium "NISSUI" (2) powder, manufactured by Nissui Pharmaceutical Co., Ltd.) supplemented with 10% fetal bovine serum (FBS) (product name: MultiSer, manufactured by Thermo Trace) and was transferred into a 1.5 mL sampling tube (500,000 cells/1 mL/tube). At the same time, 0.1 mL of each of the samples (sample 1, sample 2-S, and sample 2-R) that had been prepared with ion-exchanged water was added such that the final concentration was 1 mg/mL. To a control, ion-exchanged water 0.1 mL was added. After cultured at 37° C., in the presence of 5% $CO_2$ for four hours, cells were harvested at 3,000 rpm and subjected to mRNA detection. From this, total RNA was extracted using TRIzol reagent (manufactured by Life Technologies Corporation) and the concentration thereof was measured by Nanodrop (manufactured by Thermo Fisher Scientific K.K.). Using a cDNA synthesis kit (product name: ReverTra Ace qPCR RT Master Mix with gDNA Remover, manufactured by Toyobo Life Science), cDNA was synthesized. A reaction liquid after the reverse transcription was diluted with Nuclease-free water so as to have a concentration of 3 ng/μL to be used as a template for real-time PCR.

In PCR, HSP70 forward primer (SEQ ID NO: 1) and HSP70 reverse primer (SEQ ID NO: 2) were used as primers. Beta 2 microglobulin gene was used as an internal control gene for correction of the HSP70 gene expression; and beta 2 microglobulin forward primer (SEQ ID NO: 3) and beta 2 microglobulin reverse primer (SEQ ID NO: 4) were used as primers therefor. Real-time PCR was carried out using a reaction kit (product name: SsoAdvanced SYBR Green Supermix, manufactured by Bio-Rad Laboratories, Inc.) by a real time PCR analysis system (product name: CFX Connect, manufactured by Bio-Rad Laboratories, Inc.). A total of 10 μL of PCR reaction liquid was subjected to a three-minute incubation at 95° C., (initial denaturation) followed by repetition of 40 cycles, each cycle of which comprised denaturation at 95° C., for 1 second and annealing at 59° C., for 10 seconds.

Using Cq value obtained by the above real time PCR analysis system, a ratio of expression level of HSP70 gene was calculated on the basis of the following calculation formula (ΔΔCt method). It is to be noted that the Cq value represents the number of reaction cycles at the time when the level of amplified gene reaches a certain predetermined level in the amplification reaction of the gene.

Cq value of control HSP70: A
Cq value of control B2M: B
Cq value of sample HSP70: C
Cq value of sample B2M: D
$\Delta Cq(control) = A - B$
$\Delta Cq(sample) = C - D$
$\Delta(\Delta Cq) = \Delta Cq(sample) - \Delta Cq(control)$
Ratio of the expression level $= 2^{-\Delta(\Delta Cq)}$ The results are shown in FIG. 1. In FIG. 1, the HSP70 mRNA expression inducing activity of the sample 1, sample 2-S, and sample 2-R was expressed as a ratio (%) to that of the control. As compared with the control, the samples 1, 2-S, and 2-R exhibited an about 3- to 9-fold increased HSP70 mRNA expression (samples 2-S and 2-R, **$p<0.01$ vs. control; sample 1, *$p=0.069$ vs. control). From this, it became apparent that hydroxymethylfurfural and the S form and R form of hydroxymethylfurfural derivatives having the following structural formula had the HSP70 inducing activity at an mRNA expression level.

[FORMULA 12]

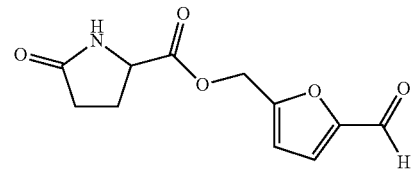

Next, with regard to the sample 1, sample 3, and sample 4, the HSP70 mRNA expression level was evaluated using human uterine cervical cancer cells (HeLa cells).

Human uterine cervical cancer cells (HeLa cells) (source: Incorporated administrative agency RIKEN, the Institute of Physical and Chemical Research, BioResource Center) were suspended in Dulbecco's Modified Eagle's Medium (DMEM) (product name: Dulbecco's Modified Eagle's Medium "Nissui" 2 powder, manufactured by Nihon Pharmaceutical Co., Ltd.) supplemented with 10% fetal bovine serum (FBS) (product name: MultiSer, manufactured by Thermo Trace) and seeded a six-well plate (200,000 cells/2 mL/well). On the following day, the medium was replaced with fresh DMEM (1.8 mL); and 0.2 mL of each of the samples was added, which samples had been each prepared with ion-exchanged water so as to have a final concentration of 1 mg/mL (with regard to the samples 3 and 4, a final concentration of 1 mg/mL in terms of a product obtained by heat-treating an asparagus stem with hot water and a product obtained by heat-treating an asparagus stem with hot water and enzyme treatment derived from the solid content of asparagus stem). To a control, ion-exchanged water 0.2 mL was added. After cultured for 22 hours, cells were scraped off with a cell scraper and subjected to mRNA detection. From this, total RNA was extracted using an RNA extraction kit (product name: Fast Pure RNA kit, manufactured by Takara Bio Inc.), diluted 100 fold with DEPC treated water; and the absorbance (wavelength 260 nm) was measured by a spectrophotometer. The RNA concentration was calculated using the calculation formula: absorbance (wavelength 260 nm)×40×dilution factor=RNA concentration (ng/μL). An RNA solution was diluted to an optional concentration with a TE buffer; and cDNA was synthesized using a cDNA synthesis kit (product name: Prime Script 1st Strand cDNA synthesis kit, manufactured by Takara Bio Inc.). Oligo dT primer (product name) (manufactured by Takara Bio Inc.)

was used as a primer. A reaction liquid after the reverse transcription was diluted with the TE buffer so as to have a concentration of 10 ng/μL to be used as a template for PCR.

In PCR, HSP70 forward primer (SEQ ID NO: 5) and HSP70 reverse primer (SEQ ID NO: 6) were used as primers. Beta 2 microglobulin gene was used as an internal control gene for correction of the HSP70 gene expression; and beta 2 microglobulin forward primer (SEQ ID NO: 3) and beta 2 microglobulin reverse primer (SEQ ID NO: 4) were used as primers therefor. For PCR, a PCR enzyme (product name: TaKaRa Ex Taq, manufactured by Takara Bio Inc.) was used. A total of 20 μL of PCR reaction liquid was subjected to a one-minute incubation at 94° C., (initial denaturation), followed by repetition of 32 cycles (HSP70) or 24 cycle (beta 2 microglobulin), each cycle of which comprised denaturation at 94° C., for 30 seconds, annealing at 57° C., (HSP70) or 59° C., (beta 2 microglobulin) for 30 seconds, and elongation at 72° C., for 30 seconds. An elongation reaction at 72° C., for 30 seconds was performed to end all PCRs. The PCR reaction liquid was electrophoresed by a conventional method; and staining with ethidium bromide was carried out.

By measuring the fluorescence intensity under ultraviolet irradiation in AlphaView (product name) (manufactured by Alpha Innotech Corporation), the HSP70 gene the expression level was measured. On this occasion, a value obtained by being corrected with the expression level of the internal control gene was regarded as the expression level of HSP70 gene.

Figure 2:
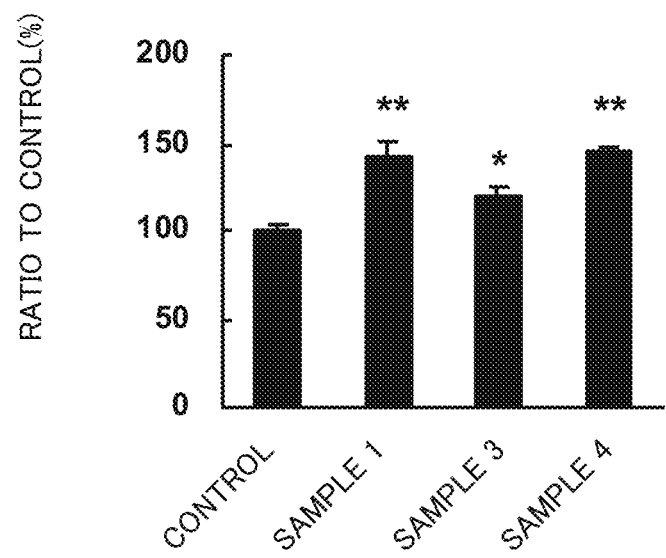
FIG. 2 is a figure showing the HSP70 mRNA expression inducing activities by hydroxymethylfurfural, a product obtained by heat-treating an asparagus stem with hot water, and a product obtained by heat-treating an asparagus stem with hot water and enzyme treatment.

The results are shown in FIG. 2. In FIG. 2, the HSP70 mRNA expression inducing activity of the samples 1, 3, and 4 was expressed as a ratio (%) to that of the control. As compared with the control, the samples 1, 3, and 4 exhibited an about 1.2- to 1.5-fold increased HSP70 mRNA expression (samples 1 and 4, **$p<0.01$ vs. control; sample 3, *$p<0.05$ vs. control). From this, it became apparent that hydroxymethylfurfural, and the product obtained by heat-treating an asparagus stem with hot water, and the product obtained by heat-treating an asparagus stem with hot water and enzyme treatment by this Example had the HSP70 inducing activity at an mRNA expression level.

Example 5

Evaluation of HSP70 Protein Expression Inducing Activity

The HSP70 inducing activity of the samples 1, 3, and 4 which were the same ones as used in Example 4 was evaluated by measuring an HSP70 protein expression level.

In the same manner as described in Example 4, HeLa cells that had been suspended in DMEM (added with 10% FBS) were seeded in a 12-well plate (100,000 cells/mL/well). On the following day, the medium was replaced with fresh DMEM (0.9 mL); and 0.1 mL of each of the samples was added, which samples had been each prepared with ion-exchanged water so as to have a final concentration of 1 mg/mL (with regard to the samples 3 and 4, a final concentration of 1 mg/mL in terms of a product obtained by heat-treating an asparagus stem with hot water and a product obtained by heat-treating an asparagus stem with hot water and enzyme treatment derived from the solid content of asparagus stem). To a control, ion-exchanged water 0.1 mL was added. After culturing for 24 hours, a culture supernatant was removed and cells were washed with PBS(−) (phosphate buffered physiological saline, pH 7.2). A part of the cells were then scraped off with a cell scraper, collected into a 1.5 mL sample tube, and subjected to HSP70 protein quantification and total protein quantification.

The quantification of HSP70 protein was carried out using HSP70 ELISA kit (product name) (manufactured by Enzo); and the quantification of total protein was carried out using Micro BCA Protein Assay Reagent kit (product name) (manufactured by PIERCE Biotechnology).

With regard to the remaining cells, an effect on cell proliferation was evaluated by 3-(4,5-dimethyl thial-2-yl)-2,5-diphenyltetrazalium bromide (MTT) method. Subsequently, a value corrected with the amount of total proteins and the number of viable cells was regarded as the amount of HSP70 protein.

Figure 3:
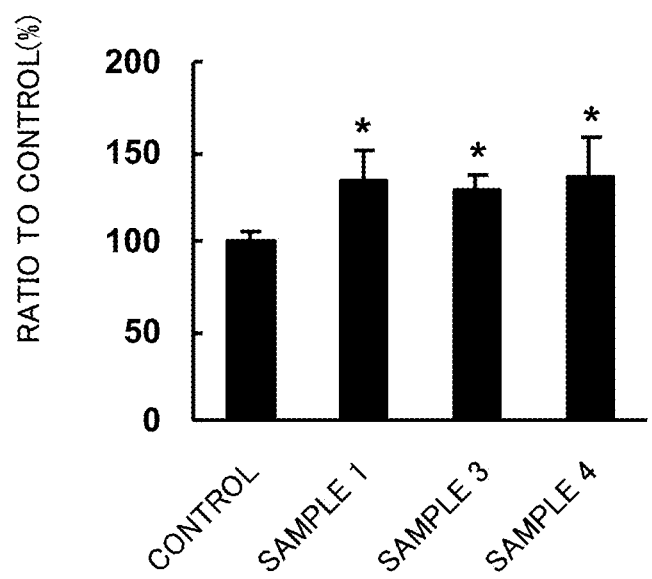
FIG. 3 is a figure showing the HSP70 protein expression inducing activities by hydroxymethylfurfural, a product obtained by heat-treating an asparagus stem with hot water, and a product obtained by heat-treating an asparagus stem with hot water and enzyme treatment.

The results are shown in FIG. 3. In FIG. 3, the HSP70 protein expression inducing activity of the samples 1, 3, and 4 was expressed as a ratio (%) to that of the control. As compared with the control, the samples 1, 3, and 4 exhibited an about 1.3-fold increased HSP70 protein expression (*$p<0.05$ vs. control). From this, it became apparent that hydroxymethylfurfural, the product obtained by heat-treating an asparagus stem with hot water, and the product obtained by heat-treating an asparagus stem with hot water and enzyme treatment by this Example had the HSP70 inducing activity at a protein expression level.

From the above, it was demonstrated that hydroxymethylfurfural, the product obtained by heat-treating an asparagus stem with hot water, and the product obtained by heat-treating an asparagus stem with hot water and enzyme treatment by this Example had an excellent HSP70 inducing activity.

Example 6

Evaluation of Anti-Stress Effect in Mouse Model of Sleep Seprivation

The anti-stress effect of the product obtained by heat-treating an asparagus stem with hot water which was obtained in Example 4 (the "sample 3" in Example 4), was evaluated using a mouse model of sleep deprivation.

Thirty two male Slc:ddY mice at 6 weeks of age (manufactured by CLEA Japan, Inc.) were divided into 4 groups (8 mice in each group). Each of the groups was designated as a normal group, a control group, a group with a low dose of the product obtained by heat-treating an asparagus stem with hot water (hereinafter, referred to as a low dose group), and a group with a high dose of the product obtained by heat-treating an asparagus stem with hot water (hereinafter, referred to as a high dose group). Starting seven days before mice were put under the stress of sleep deprivation, a powder containing the product obtained by heat-treating an asparagus stem with hot water was added to regular mash feed (product name: CE-2, manufactured by CLEA Japan, Inc.) and fed everyday to mice in the low dose group at a dose of 200 mg/kg (in terms of the product obtained by heat-treating an asparagus stem with hot water derived from the solid content of asparagus stem) and to mice in the high dose group at a dose of 1000 mg/kg (in terms of the same). The normal group and control group were fed the regular mash feed. In the control group, low dose group, and high dose group, mice were immersed in water for 12 hours (8:00 to 20:00) per day to apply the stress of sleep deprivation over 3 days. To the normal group, the stress of sleep deprivation was not applied.

The anti-stress effect was evaluated in mice on the day following the last load of the stress of sleep deprivation by measuring (1) lipid peroxide levels in the blood serum (a ratio of the amount of lipid peroxide (LPO) to the amount of triglyceride (TG) in the blood serum (LPO/TG)) as an oxidative stress index, (2) measuring the blood concentration of corticosterone which is known as a stress hormone, and (3) evaluating the incidence rate of mice with hair loss.

Figure 4:
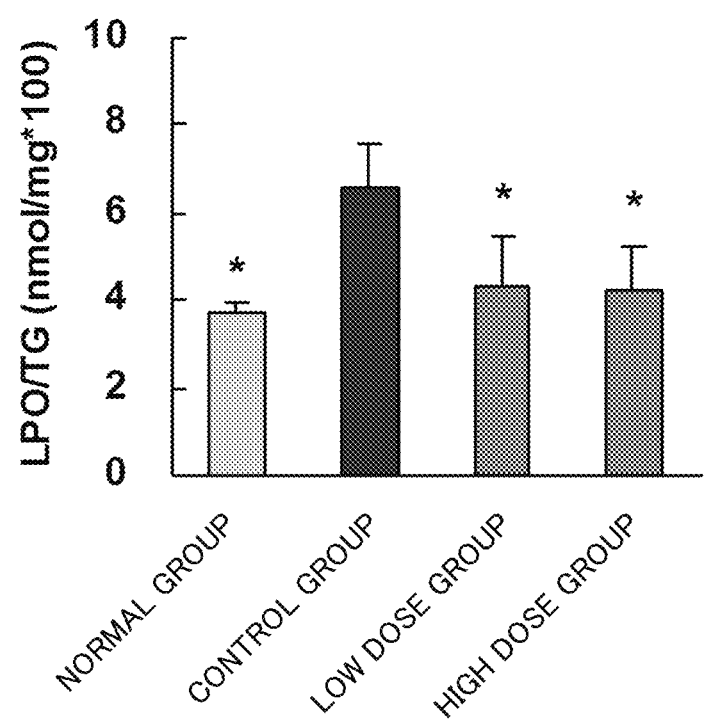
FIG. 4 is a figure showing changes in lipid peroxide levels in the blood serum by administration of a product obtained by heat-treating an asparagus stem with hot water in a mouse model of sleep deprivation.

FIG. 4 shows the result of measurement of the lipid peroxide level in the blood serum. In the figure, a higher value of LPO/TG indicates a state of a higher oxidative stress in the blood. The value of LPO/TG was high in the control group whereas the value of LPO/TG decreased to the almost same level as the normal group in the low dose group and high dose group (*$p<0.05$ vs. control). From this, it was shown that when the product obtained by heat-treating an asparagus stem with hot water by this Example was taken by mice with a state where the oxidative stress in the blood was high because of load of the stress of sleep deprivation, the oxidative stress in the blood was reduced to the level at which the stress of sleep deprivation was not applied.

Figure 5:
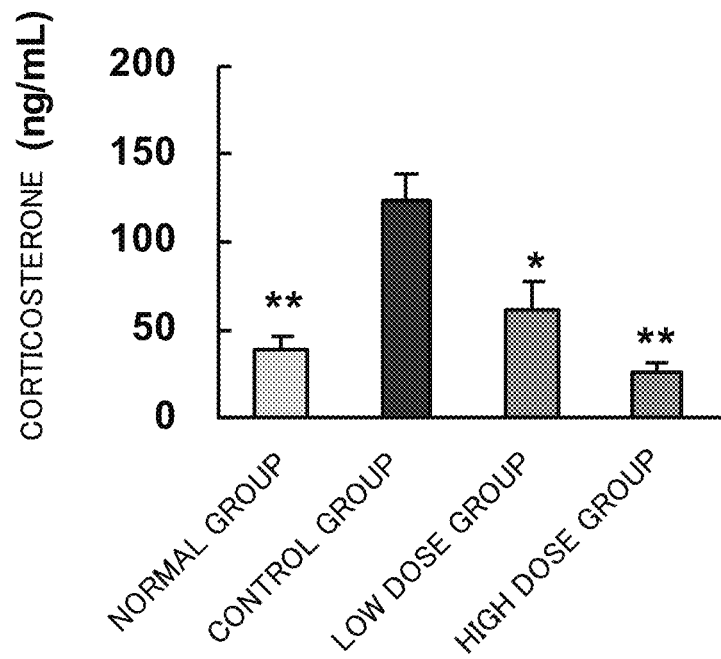
FIG. 5 is a figure showing changes in corticosterone concentration in the blood by administration of a product obtained by heat-treating an asparagus stem with hot water in a mouse model of sleep deprivation.

FIG. 5 shows the result of measurement of the corticosterone concentration in the blood. In the figure, a higher value of corticosterone concentration indicates a higher stress state. The value of corticosterone concentration was high in the control group whereas the value of corticosterone concentration decreased to the almost same level as the normal group in the low dose group and the value of corticosterone concentration was reduced to the same or lower level than the normal group in the high dose group (**$p<0.01$ vs. control, *$p<0.05$ vs. control). From this, it was shown that when the product obtained by heat-treating an asparagus stem with hot water by this Example was taken by mice that were in a higher stress state because of load of the stress of sleep deprivation, the higher stress state was reduced to the level at which the stress of sleep deprivation was not applied and, in the high dose group, reduced further to the same or lower level than the stress of sleep deprivation was not applied.

Figure 6:
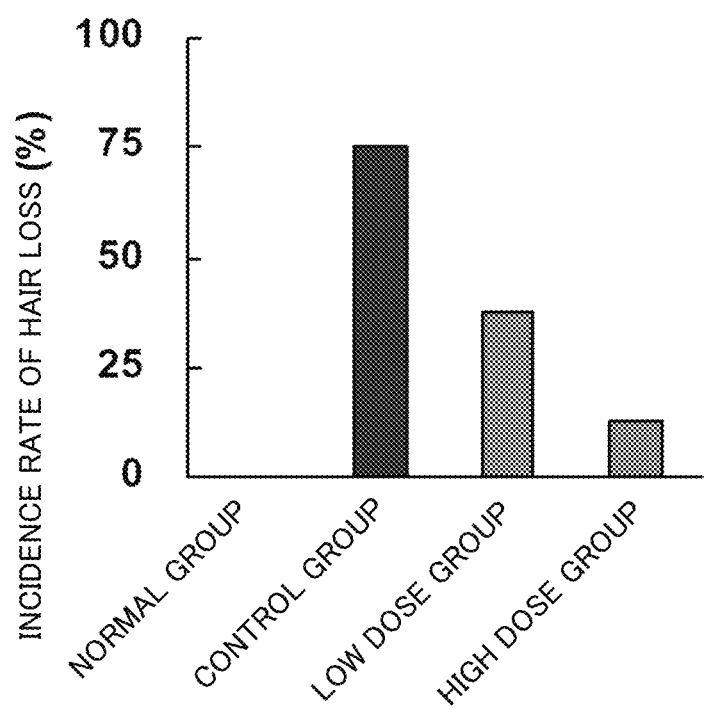
FIG. 6 is a figure showing changes in an incidence rate of hair loss by administration of a product obtained by heat-treating an asparagus stem with hot water in a mouse model of sleep deprivation.

FIG. 6 shows the incidence rate of mice with hair loss. In the figure, a higher incidence rate of hair loss indicates a higher stress state. The incidence rate of hair loss in the normal group, control group, low dose group, and high dose group was 0%, 75.0%, 37.5%, and 12.5%, respectively; and the incidence rate of hair loss was lower in the low dose group and high dose group, as compared with that of the control group. From this, it was shown that when the product obtained by heat-treating an asparagus stem with hot water by this Example was taken by mice that were in a higher stress state because of load of the stress of sleep deprivation, the higher stress state was reduced.

From the above, it was demonstrated that the product obtained by heat-treating an asparagus stem with hot water containing the hydroxymethylfurfural derivative by this Example had an excellent anti-stress effect.

Example 7

Evaluation of HSP70 Protein Expression Inducing Activity in a Mouse Model of Sleep Deprivation Using the mice used in Example 6, the HSP70 inducing activity of the product obtained by heat-treating an asparagus stem with hot water which was obtained in Example 4 (the "sample 3" in Example 4) was evaluated by measuring the HSP70 protein expression level in the stomach, liver, and kidney.

On the last day of the study in Example 6, the mice in each of the groups were sacrificed; and the stomach, liver, and kidney were each harvested. Each of the organs (50 mg) was placed in a 1.5 mL sample tube; and 500 μL of the extraction reagent of HSP70 ELISA kit (product name) (manufactured by Enzo) added with Protease inhibitor cocktail (product name) (manufactured by Sigma) at 0.2% (v/v) was added thereto. Each of the organ was then mashed on ice using a pestle rod and centrifuged at 4° C., at 1,500 rpm for 30 minutes, and the supernatant was collected. This supernatant was subjected to the quantification of HSP70 protein and the quantification of total proteins.

In the same manner as described in Example 5, the quantification of HSP70 protein was carried out using HSP70 ELISA kit (product name) (manufactured by Enzo) and the quantification of total proteins was carried out using Micro BCA Protein Assay Reagent kit (product name) (manufactured by PIERCE Biotechnology). A value corrected with the amount of total proteins was regarded as the amount of HSP70 protein.

Figure 7:
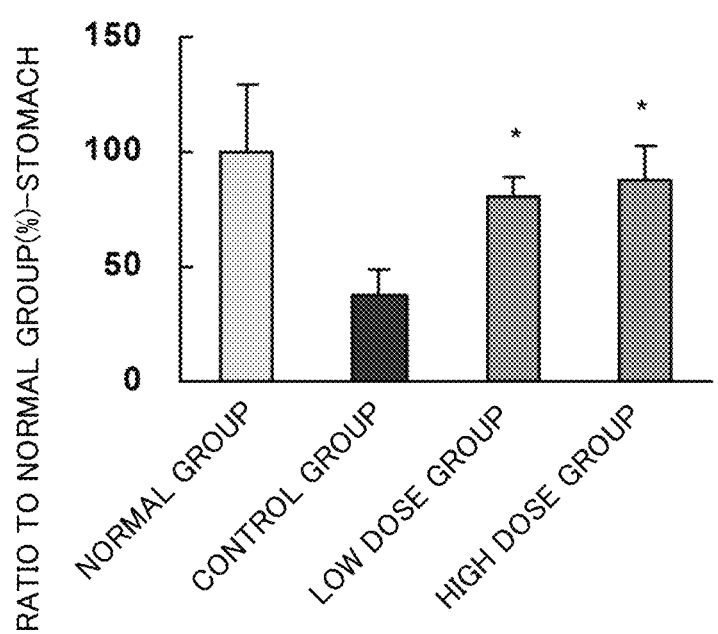
FIG. 7 is a figure showing changes in the expression level of HSP70 protein by administration of a product obtained by heat-treating an asparagus stem with hot water in the stomach of a mouse model of sleep deprivation.
Figure 8:
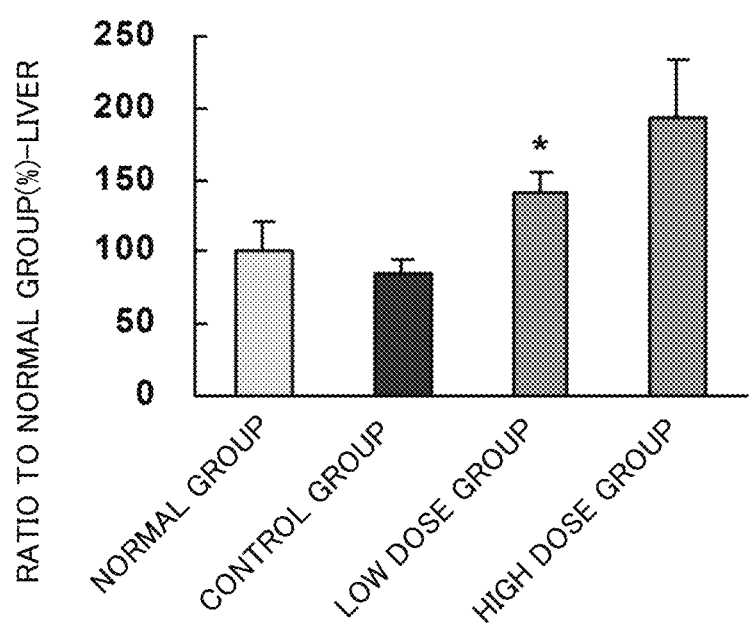
FIG. 8 is a figure showing changes in the expression level of HSP70 protein by administration of a product obtained by heat-treating an asparagus stem with hot water in the liver of a mouse model of sleep deprivation.
Figure 9:
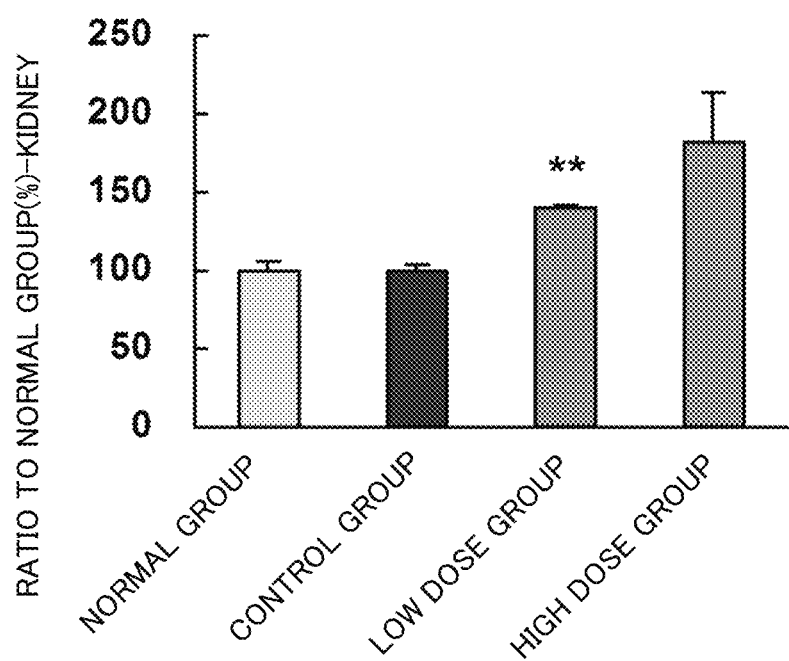
FIG. 9 is a figure showing changes in the expression level of HSP70 protein by administration of a product obtained by heat-treating an asparagus stem with hot water in the kidney of a mouse model of sleep deprivation.

FIGS. 7 to 9 show the expression level of the HSP70 protein in the stomach, liver, and kidney. In FIGS. 7 to 9, the HSP70 protein expression inducing activity of the control group, low dose group, and high dose group was expressed as a ratio (%) to that of the normal group. In the stomach (FIG. 7) and liver (FIG. 8), the expression level of HSP70 protein decreased in the control group as compared with the normal group; whereas the HSP70 protein expression increased in the low dose group and high dose group to the same or higher level than that in the normal group (*$p<0.05$ vs. control). In the kidney (FIG. 9), the HSP70 protein expression increased in the low dose group and high dose group, as compared with the control group (**$p<0.01$ vs. control).

From the above, it became apparent that the product obtained by heat-treating an asparagus stem with hot water containing the hydroxymethylfurfural derivative by this Example had, even when administrated to animals, an excellent HSP70 inducing activity at a protein expression level. Further, it was suggested that one of the mechanisms of action of the anti-stress effect shown in Example 6 was the HSP70 expression inducing activity of the product obtained by heat-treating an asparagus stem with hot water containing the hydroxymethylfurfural derivative by this Example.

Example 8

Evaluation of HSP70 mRNA Expression Inducing Activity in Human

Using the product obtained by heat-treating an asparagus stem with hot water which was obtained in Example 4 (the "sample 3" in Example 4), an HSP70 inducing activity in human white blood cells was evaluated by measuring an HSP70 mRNA expression level.

Three volunteers who voluntarily expressed intent to participate were employed as subjects (hereinafter, referred to as subject 1, subject 2, and subject 3). A powder containing product obtained by heat-treating an asparagus stem with hot water was taken twice a day (morning and evening) for 3 days, by the subject 1 at a dose of 200 mg/day, the subject 2 at a dose of 400 mg/day, and the subject 3 at a dose of 800 mg/day, (in 200 mg (subject 1), 400 mg (subject 2), and 800 mg (subject 3) of such a powder of the product obtained by heat-treating an asparagus stem with hot water, 98 mg, 197 mg, and 394 mg of the product obtained by heat-treating an asparagus stem with hot water derived from the solid content of asparagus stem were contained, respectively).

Before the start of the intake and on the last day of the intake, the blood was drawn and the expression level of HSP70 mRNA in white blood cells was measured. The blood 1 mL was mixed with 10 mL of ACK buffer solution (0.15 M ammonium chloride, 1.0 mM potassium bicarbonate, 0.1 mM EDTA-2Na, pH 7.2) at 37° C., and kept at 37° C., for 10 minutes. The resultant was then centrifuged at 3,000 rpm for 5 minutes and the supernatant was removed. The precipitated white blood cells were again added with 10 mL of ACK buffer solution to be suspended. The same procedure was repeated three times; and Trizol reagent (product name) (Life Technologies) 1.5 mL was added to the precipitated white blood cells to extract total RNA. Procedures subsequent to this, including a PCR reaction, were carried out in the same manner as described in Example 4 (the evaluation in HeLa cells); and the expression amount of HSP70 mRNA was evaluated.

Figure 10:
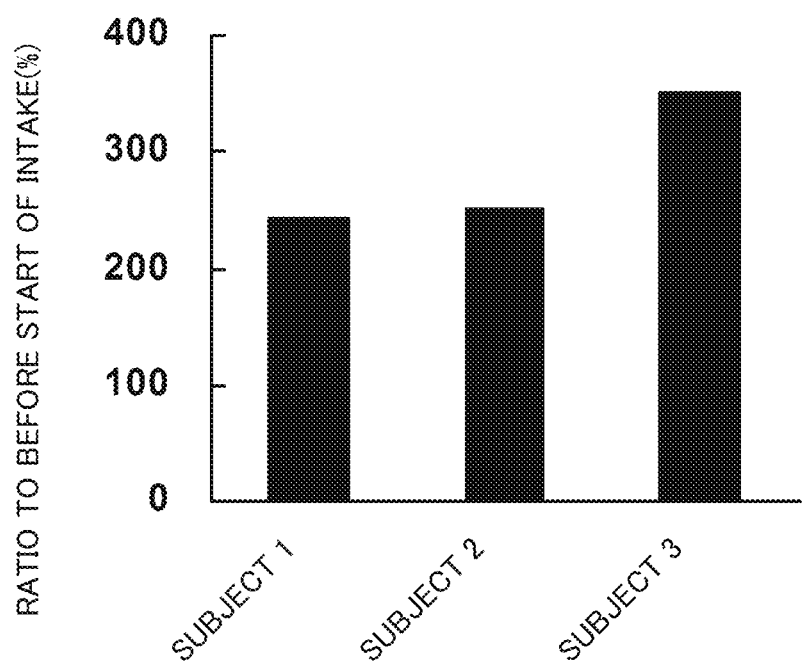
FIG. 10 is a figure showing changes in the expression level of HSP70 mRNA by administration of a product obtained by heat-treating an asparagus stem with hot water in human.

The results are shown in FIG. 10. In FIG. 10, a ratio (%) of the expression level of HSP70 mRNA in the white blood cells after the completion of the intake to that before the start of the intake is presented. The HSP70 mRNA expression in the white blood cells after the completion of the intake increased about 2.5 to 3.5 fold in a fashion dependent on the dose of the product obtained by heat-treating an asparagus stem with hot water, as compared with that before the start of the intake.

From the above, it became apparent that the product obtained by heat-treating an asparagus stem with hot water containing the hydroxymethylfurfural derivative by this Example had, even when administrated in human, an excellent HSP70 inducing activity at an mRNA expression level.

Example 9

Clinical Evaluation of Autonomic Nerve Regulatory Effect of a Product Obtained by Heat-Treating an Asparagus Stem with Hot Water Using the product obtained by heat-treating an asparagus stem with hot water which was obtained in Example 4 (the "sample 3" in Example 4), an autonomic nerve regulatory effect in human was evaluated.

Thirty volunteers who voluntarily expressed intent to participate were employed as subjects to carry out a randomized placebo controlled double blind study. The subjects were allocated, by using a lottery, to a placebo group (hereinafter, referred to as P group) 15 subjects, or a group with the product obtained by heat-treating an asparagus stem with hot water (hereinafter, referred to as A group) 15 subjects. Over four weeks during the study period, the subjects in the P group took an excipient (product name: Pinedex, manufactured by Matsutani Chemical Industry Co., Ltd.) (400 mg/day) whereas the subjects in the A group took a powder containing the product obtained by heat-treating an asparagus stem with hot water (400 mg/day) twice a day (morning and evening) everyday (in 400 mg of such a powder of the product obtained by heat-treating an asparagus stem with hot water, the product obtained by heat-treating an asparagus stem with hot water derived from the solid content of asparagus stem accounted for 197 mg and the remaining 203 mg was the excipient (same as above)).

Before the start of the study and on the last day of the study, an autonomic nervous balance and autonomic nervous activity were evaluated using an acceleration pulse wave inspection system (product name; Pulse analyzer plus TAS-9, manufactured by YKC Corporation). Such a system is a system in which acceleration pulse waves are measured at the fingertip to thereby detect subtle changes in the heart rate (Heart Rate Variability: HRV) and evaluate autonomic nerve functions. HRV is expressed as clinical consequences for various influences that the autonomic nerve brings about to the heart rate. The autonomic nervous balance was evaluated by plotting an index for sympathetic nerve activity (Low Frequency: LF) on the X axis and an index for parasympathetic nerve activity (High Frequency: HF) on the Y axis, which activities were given by such a system, to prepare a two-dimensional graph, and using a distance between the point at which the autonomic nervous balance was best and the point at a measured value on such a graph. Meanwhile, with regard to the autonomic nervous activity, numerical values representing the activity of the autonomic nerve that was given by such a system (the numerical values being calculated using LF, HF, and the like by such a system) were used.

Figure 11:
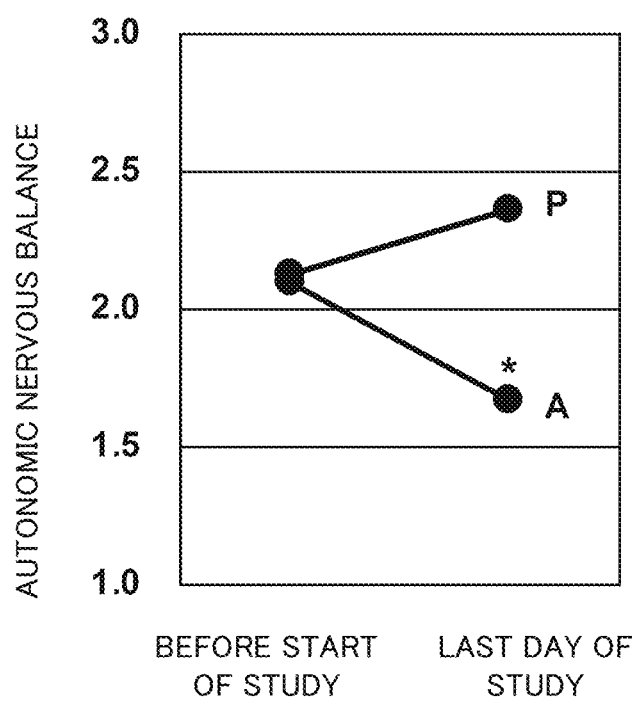
FIG. 11 is a figure showing changes in autonomic nervous balance by administration of a product obtained by heat-treating an asparagus stem with hot water in human.

FIG. 11 shows changes in the autonomic nervous balance. In the figure, a closer numerical value to zero indicates a better balance of the autonomic nerve. In the P group (the placebo group), the balance of the autonomic nerve on the last day of the study worsened, as compared with that before the start of the study. On the other hand, in the A group (the group with the product obtained by heat-treating an asparagus stem with hot water), the balance of the autonomic nerve on the last day of the study significantly improved, as compared with that before the start of the study (*p<0.05 vs. before the start of the study, p<0.01 vs. the placebo group). From this, it was demonstrated that, by taking the product obtained by heat-treating an asparagus stem with hot water by this Example, the balance of the autonomic nerve improved.

Figure 12:
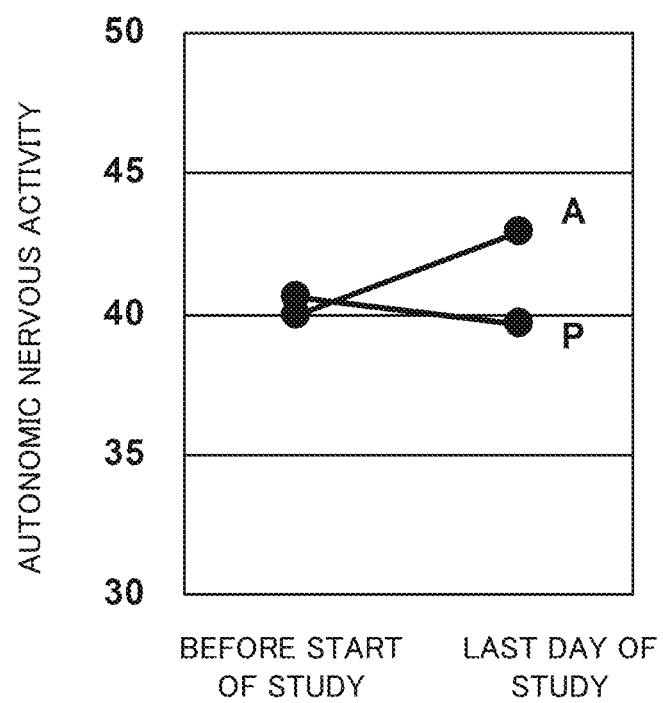
FIG. 12 is a figure showing changes in autonomic nervous activity by administration of a product obtained by heat-treating an asparagus stem with hot water in human.

FIG. 12 shows changes in the autonomic nervous activity. In the figure, a higher numerical value indicates a higher autonomic nervous activity. In the P group (the placebo group), a decreased autonomic nervous activity was found on the last day of the study, as compared with that before the start of the study. On the other hand, in the A group (the group with the product obtained by heat-treating an asparagus stem with hot water), an elevated autonomic nervous activity was found on the last day of the study, as compared with that before the start of the study. From this, it was demonstrated that, by taking the product obtained by heat-treating an asparagus stem with hot water by this Example, the autonomic nervous activity improved.

From the above, it was demonstrated that the product obtained by heat-treating an asparagus stem with hot water containing the hydroxymethylfurfural derivative by this Example had an excellent autonomic nerve regulatory effect.

Example 10

Evaluation of HSP70 mRNA Expression Inducing Activity of a Product Obtained by Heat-Treating an Asparagus Stem with Hot Water and Enzyme Treatment in Human and Clinical Evaluation of Autonomic Nerve Regulatory Effect Thereof Using the obtained capsule filled with the product obtained by heat-treating an asparagus stem with hot water and enzyme treatment, evaluation of an HSP70 mRNA expression inducing activity in human and clinical evaluation of an autonomic nerve regulatory effect were carried out as described below.

(Method of Producing a Capsule Filled with a Product Obtained by Heat-Treating an Asparagus Stem with Hot Water and Enzyme Treatment)

A method for producing a capsule filled with a product obtained by heat-treating an asparagus stem with hot water and enzyme treatment for human intake is shown below. To green asparagus stems (fresh weight 130 kg), water 170 L was added; and the mixture was, for the purpose of heat treatment with hot water, subjected to heat sterilization (100° C., 45 minutes). After allowed to cool to 45° C., the resultant was added with 3.0 kg of enzymes (Sumizyme C and Sumizyme MC; manufactured by Yakult Pharmaceutical Industry Co., Ltd.) and stirred at 45° C., for 24 hours. The enzymes were then deactivated (100° C., 20 minutes); and centrifugation was carried out. The resultant was concentrated by an evaporator, added with 9.0 kg of excipient (product name: Pinedex, manufactured by Matsutani Chemical Industry Co., Ltd.), and autoclaved (121° C., 45 minutes). Subsequently, by spray drying, a powder containing the product obtained by heat-treating an asparagus stem with hot water and enzyme treatment 16.0 kg (in this, the product obtained by heat-treating an asparagus stem with hot water and enzyme treatment derived from the solid content of asparagus stem accounted for 7.0 kg and the excipient accounted for 9.0 kg) was obtained. This powder containing the product obtained by heat-treating an asparagus stem with hot water and enzyme treatment 8.50 kg was mixed with an anticaking agent (product name: Calcium stearate, manufactured by Sun Ace Corporation) 1.86 kg and cellulose (product name: Ceolus, manufactured by Asahi Kasei Corp.) 8.20 kg to prepare a powder for capsules containing 20% the product obtained by heat-treating an asparagus stem with hot water and enzyme treatment derived from the solid content of asparagus stem. One obtained by filling this powder for capsules in No. 1 capsule at 280 mg per capsule was used as to a capsule filled with the product obtained by heat-treating an asparagus stem with hot water and enzyme treatment.

(Method of Evaluation)

Twenty volunteers who voluntarily expressed intent to participate were employed as subjects; and a short term randomized placebo controlled double blind study was carried out at a low dose. The subjects were randomly allocated to a placebo group (hereinafter, referred to as P group) 10 subjects or a group with a product obtained by heat-treating an asparagus stem with hot water and enzyme treatment (hereinafter, referred to as E group) 10 subjects. Over one week during the study period, the subjects in the P group took a placebo capsule (a total of 840 mg of mixture of product name: Pinedex (manufactured by Matsutani Chemical Industry Co., Ltd.) 699.9 mg and product name: Malt extract (Oriental Kogyo) 140.1 mg (3 capsules)/day) everyday whereas the subjects in the E group took the capsule filled with the product obtained by heat-treating an asparagus stem with hot water and enzyme treatment (840 mg (3 capsules)/day) after dinner every day (in 840 mg of such a capsule filled with product obtained by heat-treating an asparagus stem with hot water and enzyme treatment, the product obtained by heat-treating an asparagus stem with hot water and enzyme treatment derived from the solid content of asparagus stem accounted for 168 mg and the remaining 672 mg was Pinedex, calcium stearate, and Ceolus). The expression amount of HSP70 mRNA in white blood cells, autonomic nervous balance, and autonomic nervous activity are employed as endpoints.

(HSP70 mRNA Expression Inducing Activity Evaluation)

First, the expression level of HSP70 mRNA in white blood cells was measured. Before the start of the study and on the last day of the study, the blood was drawn; and total RNA was extracted from 400 μL of the blood using an RNA extraction kit (product name: Nucleo Spin RNA Blood, manufactured by Takara Bio Inc.). The method of cDNA synthesis and PCR conformed to the method described in Example 8.

Figure 13:
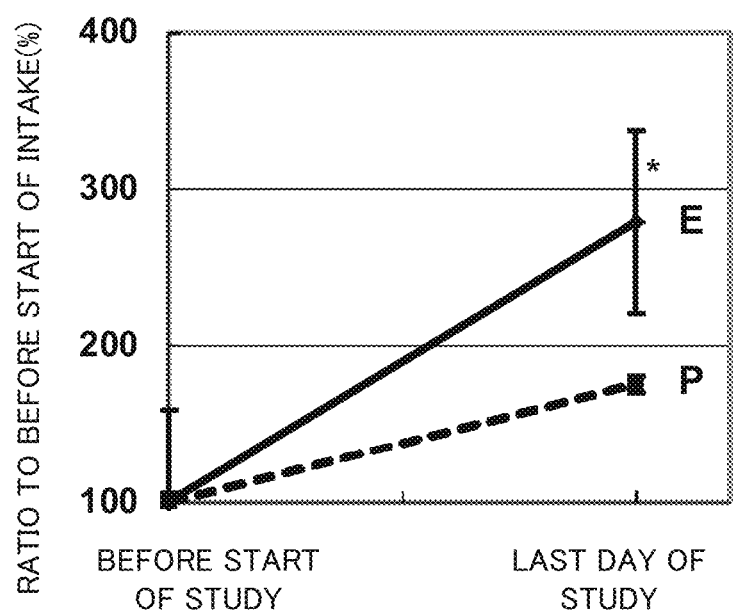
FIG. 13 is a figure showing changes in the expression level of HSP70 mRNA by administration of a product obtained by heat-treating an asparagus stem with hot water and enzyme treatment in human.

The results are shown in FIG. 13. In FIG. 13, a ratio (%) of the expression level of HSP70 mRNA in the white blood cells after the completion of the intake to that before the start of the intake is presented. The expression level of HSP70 mRNA in the P group (the placebo group) was, on the basis of the average value, 175% of that before the start of the intake. On the other hand, the expression level of HSP70 mRNA in the E group (the group with the product obtained by heat-treating an asparagus stem with hot water and enzyme treatment) was, on the basis of the average value, 278% of that before the start of the intake; and the expression increased (*p=0.098 vs. the P group). From this, it was demonstrated that, by taking the product obtained by heat-treating an asparagus stem with hot water and enzyme treatment by this Example, the expression amount of HSP70 mRNA increased markedly.

(Clinical Evaluation on Autonomic Nerve Regulatory Effect)

Next, the autonomic nervous balance and autonomic nervous activity were evaluated using an acceleration pulse wave inspection system (product name; Pulse analyzer plus TAS-9, manufactured by YKC Corporation) before the start of the study and on the last day of the study. The details of measurement were the same as described in Example 9.

Figure 14:
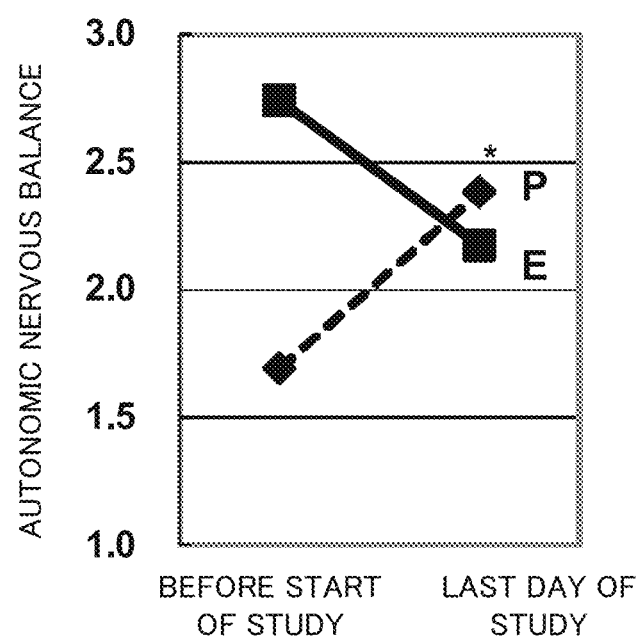
FIG. 14 is a figure showing changes in autonomic nervous balance by administration of a product obtained by heat-treating an asparagus stem with hot water and enzyme treatment in human.

FIG. 14 shows changes in the autonomic nervous balance. In the P group (the placebo group), the autonomic nervous balance on the last day of the study significantly worsened, as compared with that before the start of the study (*p<0.05 vs. before the start of the study). On the other hand, in the E group (the group with the product obtained by heat-treating an asparagus stem with hot water and enzyme treatment), the balance of the autonomic nerve on the last day of the study improved, as compared with that before the start of the study. From this, it was demonstrated that, by taking the product obtained by heat-treating an asparagus stem with hot water and enzyme treatment by this Example, the balance of the autonomic nerve improved.

Figure 15:
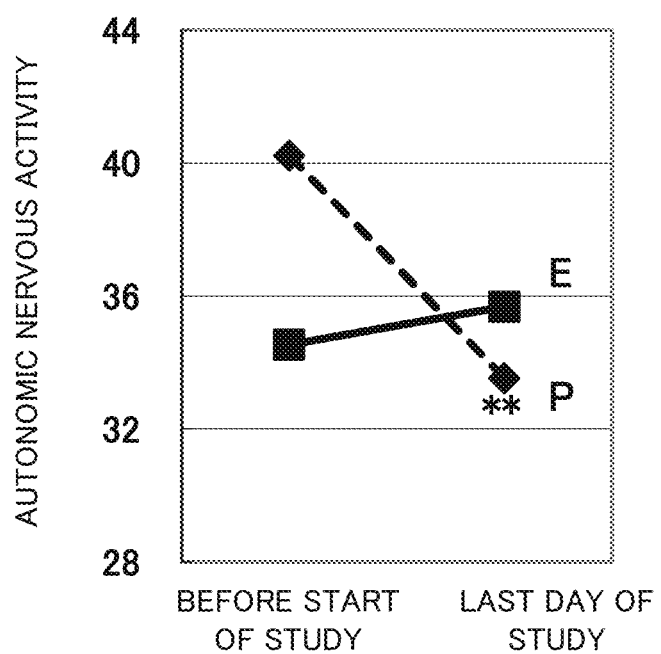
FIG. 15 is a figure showing changes in an autonomic nervous activity by administration of a product obtained by heat-treating an asparagus stem with hot water and enzyme treatment in human.

FIG. 15 shows changes in the autonomic nervous activity. In the P group (the placebo group), the autonomic nervous activity on the last day of the study significantly worsened, as compared with that before the start of the study (**p<0.01 vs. before the start of the study). On the other hand, in the E group (the group with the product obtained by heat-treating an asparagus stem with hot water and enzyme treatment), the autonomic nervous activity on the last day of the study improved, as compared with that before the start of the study. From this, it was demonstrated that, by taking the product obtained by heat-treating an asparagus stem with hot water and enzyme treatment by this Example, deterioration of the autonomic nervous activity was prevented.

As described above, according to the present disclosure, a novel hydroxymethylfurfural derivative, a highly effective pharmaceutical, HSP inducer, anti-stress agent, and autonomic nerve regulator can be provided. In addition, foods and drinks having an excellent HSP inducing activity, anti-stress effect, and autonomic nerve regulatory effect can be provided. Further, a method of producing a hydroxymethylfurfural derivative that can reduce the cost and is simple and convenient can be provided.

It is to be noted that various embodiments and modifications are feasible in the present disclosure without departing from the broad spirit and scope of the present disclosure. Further, the above-mentioned embodiments are intended to illustrate the present disclosure and are not intended to limit the scope of the present disclosure. That is, the scope of the present disclosure is indicated by the claims rather than by the embodiments. And various modifications which come within the claims and within the meaning of invention equivalent to the claims are deemed to be within the scope of the present disclosure.

We claim:

1. A method for induction of a heat shock protein, anti-stress, or regulation of an autonomic nerve comprising administering a mammalian subject in need thereof once or twice daily a composition comprising an effective amount of hydroxymethylfurfural derivative of the following formula:

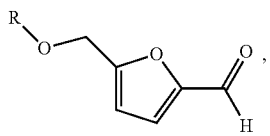

wherein R is selected from the group consisting of formula (I):

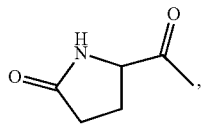

(II): HOOCCH$_2$COCO—, and (III): HOOCCH$_2$CH$_2$COCO—, at a dosage of 50 mg to 2000 mg per day, wherein the dosage is in a form selected from the group consisting of granules, particulates, tablets, capsules, suspensions, aqueous solutions, emulsions, and powders.

2. The method according to claim 1 wherein the hydroxymethylfurfural derivative is obtained by heat-treating an asparagus stem with hot water and an enzyme treatment,
wherein the enzyme treatment is carried out by adding at least one enzyme selected from among a group consisting of cellulase, hemicellulase, pectinase, amylase and pullulanase; and treating at a temperature of 30 to 60° C., for 1 to 72 hours.

3. The method of claim 1 wherein the composition comprises powders prepared by a method comprising: heat-treating an asparagus stem with hot water to obtain a heat-treated mixture for about 20 to 180 minutes; cooling; filtering; concentrating; adding a pharmaceutically acceptable excipient; and drying.

4. The method of claim 1 wherein the dosage is in a form selected from the group consisting of tablets, capsules, suspensions, aqueous solutions, emulsions, and powders.

5. A method for induction of a heat shock protein, anti-stress, or regulation of an autonomic nerve comprising:
heat-treating an asparagus stem with hot water and an enzyme treatment, wherein the enzyme treatment is carried out by adding at least one enzyme selected from the group consisting of cellulase, hemicellulase, pectinase, amylase, and pullulanase, at a temperature of 30° C. to 60° C. for 1 to 72 hours,
administering the resulting product to a mammalian subject in need thereof, and
evaluating heat shock protein activity, stress, autonomic nervous balance, or autonomic nervous activity of the mammalian subject.

6. The method of claim 5 wherein the product is in a form selected from the group consisting of granules, particulates, tablets, capsules, suspensions, aqueous solutions, emulsions, and powders, and administered once or twice daily at a dosage of 50 mg to 2000 mg per day.

7. The method of claim 6 wherein the product is in a form selected from the group consisting of tablets, capsules, suspensions, aqueous solutions, emulsions, and powders.

8. A method for induction of a heat shock protein, anti-stress or regulation of an autonomic nerve comprising:
administering a mammalian subject in need thereof a composition comprising an effective amount of hydroxymethylfurfural derivative of the following formula:

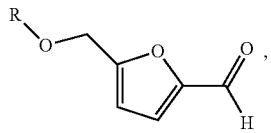

wherein R is selected from the group consisting of formula (I):

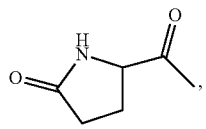

(II): HOOCCH$_2$COCO—, and (III): HOOCCH$_2$CH$_2$COCO—, and
evaluating heat shock protein activity, stress, autonomic nervous balance, or autonomic nervous activity of the mammalian subject.

9. The method of claim 8 wherein the evaluating step is conducted at least once before the administrating step and at least once after the administrating step.

10. The method of claim 8 wherein the administrating step comprises administrating the mammalian subject the composition 50 mg to 2000 mg/day.

11. The method of claim 8 wherein the administrating step comprises administrating the mammalian subject the composition once or twice daily.

12. The method of claim 8 wherein the composition is in a dosage form selected from the group consisting of granules, particulates, tablets, capsules, suspensions, aqueous solutions, emulsions, and powders.

13. The method according to claim 8 wherein the composition is in a dosage form selected from the group consisting of tablets, capsules, suspensions, aqueous solutions, emulsions, and powders.

14. The method according to claim 8 wherein the hydroxymethylfurfural derivative is obtained by heat-treating an asparagus stem with hot water and an enzyme treatment,
wherein the enzyme treatment is carried out by adding at least one enzyme selected from among a group consisting of cellulase, hemicellulase, pectinase, amylase and pullulanase; and
treating at a temperature of 30 to 60° C., for 1 to 72 hours.

15. The method of claim 8 wherein the composition comprises powders prepared by a method comprising: heat-treating an asparagus stem with hot water to obtain a heat-treated mixture for about 20 to 180 minutes; cooling; filtering; concentrating; adding an pharmaceutically acceptable excipient; and drying.

* * * * *